(12) United States Patent
Hatta et al.

(10) Patent No.: US 8,361,625 B2
(45) Date of Patent: Jan. 29, 2013

(54) INTERLAYER FILM FOR LAMINATED GLASS AND LAMINATED GLASS

(75) Inventors: Bungo Hatta, Koka (JP); Hirofumi Kitano, Koka (JP); Minoru Inada, Koka (JP); Jun Hikata, Osaka (JP)

(73) Assignees: Sekisui Chemical Co., Ltd., Osaka (JP); Orient Chemical Industries, Ltd., Osaka (JP); Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/445,566

(22) PCT Filed: Jan. 22, 2009

(86) PCT No.: PCT/JP2009/050975
§ 371 (c)(1),
(2), (4) Date: Sep. 8, 2009

(87) PCT Pub. No.: WO2009/093655
PCT Pub. Date: Jul. 30, 2009

(65) Prior Publication Data
US 2010/0279150 A1 Nov. 4, 2010

(30) Foreign Application Priority Data

Jan. 23, 2008 (JP) ................................ 2008-012819
Sep. 5, 2008 (JP) ................................ 2008-228027

(51) Int. Cl.
*B32B 17/10* (2006.01)
*B32B 27/42* (2006.01)
*C08K 5/3417* (2006.01)

(52) U.S. Cl. ........ 428/436; 428/437; 428/441; 428/442; 428/524; 428/525; 524/94

(58) Field of Classification Search .................. 428/436, 428/437, 441, 442, 524, 525; 524/94
See application file for complete search history.

(56) References Cited

U.S. PATENT DOCUMENTS

| 5,296,519 A | 3/1994 | Otsuka |
| 5,401,438 A | 3/1995 | Otsuka |
| 6,903,152 B2 * | 6/2005 | Toyama et al. ............ 524/403 |
| 2004/0234778 A1 | 11/2004 | Fukatani et al. |
| 2006/0110593 A1 * | 5/2006 | Fukatani et al. ........... 428/328 |

FOREIGN PATENT DOCUMENTS

| EP | 0477844 | 4/1992 |
| JP | 04-134065 | 5/1992 |
| JP | 08-259708 | 10/1996 |
| JP | 08-287715 | 11/1996 |
| JP | 2000-300149 | 10/2000 |
| JP | 2002-097041 | 4/2002 |
| JP | 2003-252657 | 9/2003 |
| JP | 2004227843 | 8/2004 |
| JP | 2005-194128 | 7/2005 |
| JP | 2007-290923 | 11/2007 |

OTHER PUBLICATIONS

Extended European Search Report issued Mar. 24, 2011 in corresponding European Application No. EP09703469.
English translation of the International Search Report issued in related International Application No. PCT/JP2009/050975.

* cited by examiner

*Primary Examiner* — D. S. Nakarani
(74) *Attorney, Agent, or Firm* — Connolly Bove Lodge & Hutz LLP

(57) ABSTRACT

An interlayer film for a laminated glass which reduces transmittance of ultraviolet rays having wavelength of 380 to 400 nm and has an excellent durability to light exposure, while maintaining high visible light transmittance. The interlayer film for a laminated glass comprises a thermoplastic resin and an indole compound having a structure represented by the following chemical formula 1:

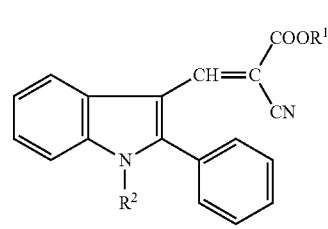

(1)

Wherein $R^1$ represents an alkyl group having 1-3 carbon atoms, and $R^2$ represents hydrogen, an alkyl group having 1-10 carbon atoms, or an aralkyl group having 7-10 carbon atoms.

31 Claims, No Drawings

INTERLAYER FILM FOR LAMINATED GLASS AND LAMINATED GLASS

This application is a national phase of PCT/JP2009/050975, filed on Jan. 22, 2009, which claims priority to Japanese Patent Application 2008-012819 filed Jan. 23, 2008 and Japanese Patent Application 2008-228027 filed Sep. 5, 2008, the entire contents of all are hereby incorporated by reference.

TECHNICAL FIELD

The present invention relates to an interlayer film for a laminated glass which can reduce transmittance of ultraviolet rays having wavelength of 380 to 400 nm and has excellent durability to light exposure while maintaining high visible light transmittance.

BACKGROUND ART

A laminated glass is a safety glass because few glass fragments are scattered even if it is broken by impact from the outside. Therefore, laminated glasses have been used widely for windowpanes of motor vehicles such as automobiles, aircrafts, buildings, and the like. Examples of laminated glasses include glasses obtained by inserting, between at least one pair of glasses, an interlayer film for a laminated glass which contains polyvinyl acetal plasticized by a plasticizer, and then by uniting them, and then by laminating them.

When laminated glasses are used as windowpanes of motor vehicles such as automobiles, aircrafts, and buildings, they are used under a condition exposed to irradiation of ultraviolet rays. A conventional interlayer film for a laminated glass contains ultraviolet absorbers so as to block ultraviolet rays. Most ultraviolet absorbers contained in interlayer films for laminated glasses block only ultraviolet rays having wavelength of 380 nm or shorter. Therefore, an interlayer film for a laminated glass containing the ultraviolet absorbers cannot sufficiently block ultraviolet rays having wavelength of 380 to 400 nm.

As an example of an interlayer film for a laminated glass to overcome the problem mentioned above, Patent Document 1 discloses an interlayer film for a laminated glass containing a synthetic resin, an ultraviolet absorber, and a yellow dye which absorbs light having wavelength of 380 to 450 nm. It is said that the interlayer film for a laminated glass disclosed in Patent Document 1 can block light having wavelength of 450 nm or shorter while maintaining lighting-transmitting properties. However, Patent Document 1 does not consider any method for homogeneously dispersing the yellow dye in the interlayer film for a laminated glass, and thus it is not possible to obtain an interlayer film for a laminated glass having high visible light transmittance. And also, the interlayer film for a laminated glass disclosed in Patent Document 1 has a problem that practically it cannot sufficiently block ultraviolet rays having wavelength of 380 to 400 nm.

And also, Patent Document 2 discloses an interlayer film containing a synthetic resin material with an organic light absorber added thereto. As examples of the organic light absorbers, ultraviolet absorbers, blue light absorbers, infrared absorbers, and red light absorbers are described. However, the organic light absorbers described in Patent Document 2 cannot sufficiently block ultraviolet rays having wavelength of 380 to 400 nm.

Patent Document 1: Japanese Kokai Publication 2000-300149 (JP-A-2000-300149)

Patent Document 2: Japanese Kokai Publication 2007-290923 (JP-A-2007-290923)

DISCLOSURE OF THE INVENTION

Problems to be Solved by the Invention

The present invention aims to provide an interlayer film for a laminated glass which is capable of reducing transmittance of ultraviolet rays having wavelength of 380 to 400 nm, and which has excellent durability to light exposure while maintaining high visible light transmittance.

Means for Solving the Problems

The present invention provides an interlayer film for a laminated glass, which contains a thermoplastic resin and an indole compound having a structure represented by the following general Chemical Formula (1).

[Chemical Formula 1]

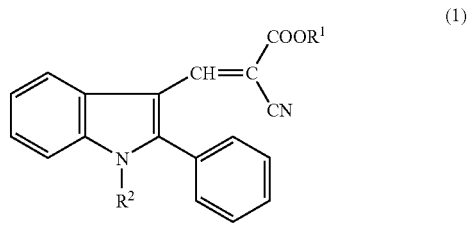

(1)

In the general Chemical Formula (1), $R^1$ represents an alkyl group having 1 to 3 of carbon atoms, and $R^2$ represents hydrogen, an alkyl group having 1 to 10 of carbon atoms, or an aralkyl group having 7 to 10 of carbon atoms.

The following description will discuss details of the present invention.

The present inventors have found that, when an interlayer film for a laminated glass contains an indole compound having a specific structure, the interlayer film can reduce transmittance of ultraviolet rays having wavelength of 380 to 400 nm while maintaining high visible light transmittance.

Laminated glasses obtained by using interlayer films containing indole compounds have a problem that, when the laminated glasses are used under exposure to sunlight, the transmittance of ultraviolet rays will increase with the passing of time, and the hue of the laminated glasses will change. The present inventors have found that the number of carbon atoms in the $R^1$ in the general Chemical Formula (1) is related to durability of the laminated glass to light exposure and that high durability to light exposure can be achieved by setting the number of carbon atoms in the $R^1$ within a certain range. In this way, the present inventors completed the present invention.

The interlayer film for a laminated glass of the present invention contains an indole compound having a structure represented by the general Chemical Formula (1). The interlayer film for a laminated glass of the present invention has high visible light transmittance and low transmittance of ultraviolet rays having wavelength of 380 to 400 nm because the interlayer film contains an indole compound having a structure represented by the general Chemical Formula (1).

In the general Chemical Formula (1), $R^1$ represents an alkyl group having 1 to 3 of carbon atoms. Examples of the $R^1$ include methyl group, ethyl group, isopropyl group, n-propyl group and the like. Among them, methyl group, ethyl group or isopropyl group are preferable, and methyl group or ethyl group are more preferable.

In the general Chemical Formula (1), $R^2$ represents hydrogen, an alkyl group having 1 to 10 of carbon atoms, or an aralkyl group having 7 to 10 of carbon atoms. Among them, the alkyl group having 1 to 10 of carbon atoms is preferable, and an alkyl group having 1 to 8 of carbon atoms is more preferable. Examples of the alkyl group having 1 to 10 of carbon atoms include methyl group, ethyl group, isopropyl group, n-propyl group, isobutyl group, n-butyl group, pentyl group, hexyl group, 2-ethylhexyl group, n-octyl group, and the like. Examples of the aralkyl group having 7 to 10 of carbon atoms include benzyl group, phenylethyl group, phenylpropyl group, phenylbutyl group, and the like. The alkyl group may be an alkyl group having a linear main chain or a branched main chain.

The number of carbon atoms in $R^1$ in the general Chemical Formula (1) has a significant influence on durability of a laminated glass to light exposure. The fewer is the number of carbon atoms in $R^1$, the higher is durability of the laminated glass to light exposure. And when the number of carbon atoms in $R^1$ is 1, durability to light exposure is the highest. $R^1$ includes at most three carbon atoms. If the number of carbon atoms is $R^1$ is greater or equal to four, ultraviolet transmittance will increase with the passing of time, or the hue of the laminated glass will change when the laminated glass is used under exposure to sunlight.

In the interlayer film for a laminated glass of the present invention, the preferable content of the indole compound having a structure represented by the general Chemical Formula (1) depends on the thickness of the interlayer film for a laminated glass. The preferable lower limit of the content of the indole compound having a structure represented by the general Chemical Formula (1) is 0.030 weight %, and the preferable upper limit is 0.145 weight % in the interlayer film. If the content of the indole compound having a structure represented by the general Chemical Formula (1) is 0.030 to 0.145 weight % in the interlayer film, the interlayer film for a laminated glass, which can reduce transmittance of ultraviolet rays having wavelength of 380 to 400 nm while maintaining high visible light transmittance, can be obtained. If the content of the indole compound having a structure represented by the general Chemical Formula (1) is 0.030 to 0.145 weight % in the interlayer film having a thickness of 760 μm, the interlayer film for a laminated glass, which can show particularly excellent effects, can be obtained.

The interlayer film for a laminated glass of the present invention contains a thermoplastic resin.

The thermoplastic resin is not limited to any particular resins. For examples, a polyvinyl acetal resin, an ethylene-vinyl acetate copolymer resin, an ethylene-acrylic copolymer resin, a polyurethane resin, a sulfur-containing polyurethane resin, a polyvinyl alcohol resin, and the like can be used. Among them, a polyvinyl acetal resin is preferable, because when mixed and formed together with a plasticizer, an interlayer film for a laminated glass capable of exerting excellent adhesion to the glass can be obtained.

The polyvinyl acetal resin is not particularly limited as long as it is a polyvinyl acetal resin obtainable by acetalizing polyvinyl alcohol with aldehyde, and a polyvinyl butyral resin is suitable. And if necessary, two or more kinds of polyvinyl acetal resins may be used together.

The preferable lower limit of an acetalization degree of the polyvinyl acetal resin is 40 mol %, and the preferable upper limit is 85 mol %. And the more preferable lower limit is 60 mol %. And the more preferable upper limit is 75 mol %.

In the case where a polyvinyl butyral resin is used as the polyvinyl acetal resin, the preferable minimum amount of the hydroxyl group is 15 mol %. And the preferable maximum amount of the hydroxyl group is 35 mol %. If the amount of the hydroxyl group is less than 15 mol %, adhesion between the interlayer film for a laminated glass and the glass may be deteriorated or the penetration resistance of the laminated glass to be obtained may be reduced. If the amount of the hydroxyl group exceeds 35 mol %, the interlayer film for a laminated glass to be obtained may become too hard.

The polyvinyl acetal resin can be prepared by acetalizing polyvinyl alcohol with aldehyde.

The polyvinyl alcohol can be normally obtained by saponifying polyvinyl acetate. Generally, polyvinyl alcohol having a saponification degree of 80 to 99.8 mol % is used.

The polymerization degree of the polyvinyl alcohol is preferably 500 in the lower limit and 4000 in the upper limit. If the polymerization degree of the polyvinyl alcohol is less than 500, the penetration resistance of the laminated glass to be obtained may be reduced. If the polymerization degree of the polyvinyl alcohol is more than 4000, the moldability of the interlayer film for a laminated glass may be deteriorated. A polymerization degree of the polyvinyl alcohol is more preferably 1000 in the lower limit and more preferably 3600 in the upper limit.

The aldehyde is not particularly limited, and generally, aldehyde having 1 to 10 of carbon atoms is suitably used. The aldehyde having 1 to 10 of carbon atoms is not particularly limited and examples thereof include n-butyl aldehyde, isobutyl aldehyde, n-valeraldehyde, 2-ethylbutyl aldehyde, n-hexyl aldehyde, n-octyl aldehyde, n-nonyl aldehyde, n-decyl aldehyde, formaldehyde, acetaldehyde, benzaldehyde and the like. Out of those examples, n-butyl aldehyde, n-hexyl aldehyde and n-valeraldehyde are preferable, and n-butyl aldehyde is more preferable. These aldehydes may be used alone or in combination of two or more kinds.

The interlayer film for a laminated glass of the present invention may contain a plasticizer.

The plasticizer is not particularly limited, and examples thereof include organic ester plasticizers such as monobasic organic acid ester and polybasic organic acid ester, phosphoric acid plasticizers such as organic phosphate plasticizer and organic phosphorous acid type plasticizer, and the like. It is preferable that the plasticizer is a liquid plasticizer.

The monobasic organic acid ester is not particularly limited, and examples thereof include glycol type esters obtained by a reaction of glycol such as triethylene glycol, tetraethylene glycol or tripropylene glycol with monobasic organic acid such as butyric acid, isobutyric acid, caproic acid, 2-ethylbutyric acid, heptylic acid, n-octylic acid, 2-ethylhexylic acid, pelargonic acid (n-nonylic acid) or decylic acid. Out of those examples, triethylene glycol dicaproate, triethylene glycol di-2-ethylbutyrate, triethylene glycol di-n-octylate and triethylene glycol di-2-ethylhexylate, and the like are preferable.

The polybasic organic acid ester is not particularly limited, and examples thereof include ester compounds of polybasic organic acids such as adipic acid, sebacic acid and azelaic acid and straight-chain or branched alcohols having 4 to 8 of carbon atoms. Out of those examples, dibutyl sebacate, dioctyl azelate, dibutyl carbitol adipate and the like are preferable.

The organic ester plasticizer is not particularly limited, and examples thereof include triethylene glycol di-2-ethylbutylate, triethylene glycol di-2-ethylhexanoate, triethylene glycol dicaprylate, triethylene glycol di-n-octanoate, triethylene glycol di-n-heptanoate, tetraethylene glycol di-n-heptanoate, tetraethylene glycol di-2-ethyl hexanoate, dibutyl sebacate, dioctyl azelate, dibutyl carbitol adipate, ethylene glycol di-2-ethylbutylate, 1,3-propylene glycol di-2-ethylbutylate, 1,4-butylene glycol di-2-ethylbutylate, 1,2-butylene glycol di-2-ethylenebutylate, diethylene glycol di-2-ethylbutylate, diethylene glycol di-2-ethyl hexanoate, dipropylene glycol di-2-ethylbutylate, triethylene glycol di-2-ethylpentanoate, tetraethylene glycol di-2-ethylbutylate, diethylene glycol dicaprylate, triethylene glycol di-n-heptanoate, tetraethylene glycol di-n-heptanoate, triethylene glycol di-2-ethylbutylate, triethylene glycol bis(2-ethylbutylate), triethylene glycol di-(2-ethyl hexanoate), triethylene glycol di-heptanoate, tetraethylene glycol di-heptanoate, dihexyl adipate, dioctyl adipate, hexylcyclohexyl adipate, diisononyl adipate, heptylnonyl adipate, dibutyl sebacate, oil-modified sebacic acid alkyd, a mixture of phosphate ester and adipate ester, a mixed adipate ester prepared by using adipate ester, alkyl alcohol having 4 to 9 of carbon atoms and cyclic alcohol having 4 to 9 of carbon atoms, and adipate ester having 6 to 8 of carbon atoms such as hexyl adipate.

The organic phosphate plasticizer is not particularly limited, and examples thereof include tributoxyethyl phosphate, isodecylphenyl phosphate, triisopropyl phosphate and the like.

At least one kind selected from the group consisting of dihexyl adipate (DHA), triethylene glycol di-2-ethylhexanoate (3GO), tetraethylene glycol di-2-ethylhexanoate (4GO), triethylene glycol di-2-ethylbutylate (3GH), tetraethylene glycol di-2-ethylbutylate (4GH), tetraethylene glycol di-heptanoate (4G7), and triethylene glycol di-heptanoate (3G7) among the aforementioned plasticizer can prevent the time course change in adhesive force between the interlayer film for a laminated glass and the glass when a metal salt of carboxylic acid having 5 or 6 of carbon atoms is included as an adhesion force controlling agent.

The plasticizer is preferably selected from triethylene glycol di-2-ethylhexanoate (3GO), triethylene glycol di-2-ethylbutylate (3GH), tetraethylene glycol di-2-ethylhexanoate (4GO), and dihexyl adipate (DHA), because they are hardly hydrolyzed. The plasticizer is more preferably tetraethylene glycol di-2-ethylhexanoate (4GO) or triethylene glycol di-2-ethylhexanoate (3GO) and particularly preferably triethylene glycol di-2-ethylhexanoate.

The content of the plasticizer in the interlayer film for a laminated glass is not particularly limited. The preferable lower limit of the content of the plasticizer in the interlayer film for a laminated glass is 30 parts by weight relative to 100 parts by weight of the thermoplastic resin. And the preferable upper limit is 70 parts by weight. If the content of the plasticizer is less than 30 parts by weight, the viscosity of a melted interlayer film for a laminated glass to be obtained is so high that deaeration properties upon producing the laminated glass may be deteriorated. If the content of the plasticizer exceeds 70 parts by weight, some separation of the plasticizer from the interlayer film for a laminated glass may occur. The more preferable lower limit of the content of the plasticizer is 35 parts by weight. And the more preferable upper limit of the content of the plasticizer is 63 parts by weight.

In the interlayer film for a laminated glass of the present invention, additives such as ultraviolet absorbers, antioxidants, light stabilizers, flame retardants, antistatic agents, adhesive strength controlling agents, moisture resistant agents, blue pigments, blue dyes, green pigments, green dyes, fluorescent whitening agents, and infrared absorbers may be contained.

Examples of the ultraviolet absorbers include a compound having benzotriazol structure and the like.

The infrared absorbers are not particularly limited as long as they have property to block infrared rays. The infrared absorbers are preferably at least one kind selected from the group consisting of tin-doped indium oxide particles, antimon-doped tin oxide particles, zinc oxide particles doped with elements other than zinc, hexaboride lanthanum particles, zinc antimonate particles, and an infrared absorber having a phthalocyanine structure.

The content of the infrared absorber is not particularly limited. The preferable lower limit of the content of the infrared absorber is 0.001 parts by weight relative to 100 parts by weight of the thermoplastic resin. And the preferable upper limit is 5 parts by weight. If the content of the infrared absorber is less than 0.001 parts by weight, the interlayer film for a laminated glass may not be able to block infrared rays. If the content of the infrared rays exceeds 5 parts by weight, transparency of the laminated glass may be deteriorated.

The interlayer film for a laminated glass of the present invention preferably has a thickness of 0.1 mm in the lower limit and a thickness of 3 mm in the upper limit. If the thickness of the interlayer film for a laminated glass is less than 0.1 mm, the penetration resistance of the laminated glass to be obtained may be reduced. If the thickness of the interlayer film for a laminated glass exceeds 3 mm, the transparency of the interlayer film for a laminated glass to be obtained may be deteriorated. The thickness of the interlayer film for a laminated glass is more preferably 0.25 mm in the lower limit and 1.5 mm in the upper limit.

The interlayer film for a laminated glass of the present invention may be an interlayer film having a single layer structure of only one resin layer. And also, the interlayer film for a laminated glass of the present invention may be an interlayer film having a multilayer laminated structure including at least two resin layers, provided that at least one of the resin layers is an indole compound-containing resin layer which contains a thermoplastic resin and an indole compound having a structure represented by the general Chemical Formula (1).

When the interlayer film for a laminated glass of the present invention has the multilayer laminated structure, it is preferable that at least the outermost layer contains the aforementioned thermoplastic resin, the aforementioned indole compound having a structure represented by the general Chemical Formula (1), and the aforementioned plasticizer. The thermoplastic resin contained in the outermost layer is preferably a polyvinyl acetal resin and more preferably a polyvinyl butyral resin.

When the interlayer film for a laminated glass of the present invention has the multilayer laminated structure in which at least the outmost layer contains the aforementioned thermoplastic resin, the aforementioned indole compound having a structure represented by the general Chemical Formula (1), and the aforementioned plasticizer, it is preferable that an intermediate layer preferably contains the thermoplastic resin and the plasticizer.

Moreover, the intermediate layer preferably contains the indole compound having a structure represented by the general Chemical Formula (1). The thermoplastic resin contained in the outermost layer and the intermediate layer is preferably a polyvinyl acetal resin and more preferably a polyvinyl butyral resin. When the thermoplastic resin is a polyvinyl acetal resin, the polyvinyl acetal resin contained in the intermediate layer preferably has a lower amount of the hydroxyl group than that in the polyvinyl acetal resin contained in the outermost layer. An example of the polyvinyl acetal resin contained in the intermediate layer includes a polyvinyl butyral resin containing 15 to 25 mol % of the amount of the hydroxyl group with an acetylation degree of 8 to 15 mol % and a butyralation degree of 60 to 71 mol %.

The interlayer film for a laminated glass of the present invention having a multilayer laminated structure can reduce transmittance of ultraviolet rays having wavelength of 380 to 400 nm and can show excellent durability to light exposure and excellent sound insulation properties, while maintaining high visible light transmittance.

The interlayer film for a laminated glass of the present invention preferably has at least 60% of visible light transmittance (Tv) when measured by a method according to JIS R 3106 in which the interlayer film having a thickness of 760 μm is sandwiched between two sheets of clear glasses having a thickness of 2.5 mm. When visible light transmittance (Tv) is less than 60%, the transparency of the laminated glass obtained by using the interlayer film for a laminated glass of the present invention may be deteriorated. The visible light transmittance (Tv) is preferably 70% or more, more preferably 75% or more, and particularly preferably 80% or more.

The apparatus for measuring the visible light transmittance (Tv) is not particularly limited, and a spectrophotometer (U-4000, manufactured by Hitachi, Ltd.) and the like may be exemplified.

The interlayer film for a laminated glass of the present invention can reduce the transmittance of ultraviolet rays having wavelength of 380 to 400 nm. The transmittance of ultraviolet rays having wavelength of 380 to 400 nm is preferably 2% or less, more preferably 1% or less, and particularly preferably 0.5% or less. The transmittance of ultraviolet rays having wavelength of 380 to 400 nm can be obtained by measuring the transmittances of ultraviolet rays at wavelength of 380 nm, 390 nm and 400 nm, and then by summing up the obtained values, and then by calculating the average value.

The apparatus for measuring the transmittance of ultraviolet rays having wavelength of 380 to 400 nm is not particularly limited, and a spectrophotometer (U-4000, manufactured by Hitachi, Ltd.) and the like may be exemplified.

As a method of producing the interlayer film for a laminated glass of the present invention, an example of the method is a method as follows: first, the plasticizer is mixed with a indole compound having a structure represented by the general Chemical Formula (1) to prepare a composition; the composition to which additives are added as needed is sufficiently kneaded with a thermoplastic resin such as a polyvinyl acetal resin; and the kneaded mixture is molded into an interlayer film for a laminated glass.

It is preferable that the production method includes a process to prepare a composition including the plasticizer and the indole compound having a structure represented by the general Chemical Formula (1) dissolved in the plasticizer, and a process to knead the composition with a thermosetting resin such as a polyvinyl acetal resin.

In the process for preparing the composition in which the indole compound having a structure represented by the general Chemical Formula (1) is dissolved in the plasticizer, it is preferable that the composition is heated to dissolve the indole compound.

The method for kneading the composition and the thermoplastic resin is not particularly limited, and an example of the method includes a method using an extruder, a kneader, a Banbury mixer, calendaring roll and the like. In the example, a method using an extruder is preferable, and a method using a two-axis extruder is more preferable because they are suitable for continuous production.

The interlayer film for a laminated glass of the present invention can reduce the transmittance of ultraviolet rays having wavelength of 380 to 400 nm while maintaining high visible light transmittance when the indole compound is contained therein. Further, the interlayer film for a laminated glass of the present invention has excellent durability to light exposure.

Moreover, the interlayer film for a laminated glass of the present invention can reduce the number of bubble under high temperature environment.

With regard to a laminated glass in which a interlayer film containing a relatively large amount of a plasticizer is used, there is a problem that generation of bubble tends to easily occur when the laminated glass is put under high temperature environment of 80 to 150° C. In this description, containing a relatively large amount of a plasticizer refers to that the content of the plasticizer is in the range from 50 parts by weight to 70 parts by weight relative to 100 parts by weight of the thermoplastic resin.

Moreover, in the case where a polyvinyl acetal resin having a low amount of the hydroxyl group is used as thermoplastic resin, generation of bubble tends to easily occur when the laminated glass is put under high temperature environment of 80 to 150° C. even though the content of the plasticizer is less than 50 parts by weight relative to 100 parts by weight of the thermoplastic resin. Especially, generation of bubble tends to easily occur when water content in a plasticizer is high.

Also, when the interlayer film for a laminated glass of the present invention has a single layer structure, it is possible to effectively prevent generation of bubble under high temperature environment even in the case where the content of the plasticizer is 50 to 70 parts by weight relative to 100 parts by weight of the thermoplastic resin. Similarly, when the interlayer film for a laminated glass of the present invention has a single layer structure, it is possible to effectively prevent generation of bubble under high temperature environment even in the case where a polyvinyl acetal resin having a low amount of the hydroxyl group is used as thermoplastic resin. Similarly, when the interlayer film for a laminated glass of the present invention has a single layer structure, it is possible to effectively prevent generation of bubble under high temperature environment even in the case where water content in a plasticizer is high. One possible reason of this effect is that the interlayer film for a laminated glass containing the indole compound contacts with the glass.

It is to be noted that the polyvinyl acetal resin having a low amount of the hydroxyl group refers to a polyvinyl acetal resin containing 25 mol % or less of the hydroxyl group. An example of the polyvinyl acetal resin having a low amount of the hydroxyl group includes a polyvinyl butyral resin containing 15 to 25 mol % of the hydroxyl group with an acetylation degree of 8 to 15 mol % and a butyralation degree of 60 to 71 mol %.

And also, in the case where the interlayer film for a laminated glass of the present invention has a multilayer structure, the number of bubble under high temperature environment can be reduced when the outermost layer of the interlayer film is the resin layer containing the indole compound.

For example, with regard to the interlayer film having a structure in which an interlayer containing the plasticizer in an amount of not less than 50 parts by weight relative to 100 parts by weight of the thermoplastic resin is sandwiched between the two outermost layers containing the plasticizer in an amount of 35 to 49 parts by weight, in the case where the outermost layers contain the indole compound having a structure represented by the general Chemical Formula (1), generation of bubble can be prevented even when the laminated glass is put under high temperature environment of 80 to 150° C.

When the interlayer film for a laminated glass of the present invention is sandwiched between two sheets of glasses and then laminated, the resulting product can be used as a laminated glass. The glass to be used for the laminated glass is not particularly limited and may be a generally used clear glass plate. Examples of the glass include inorganic glass such as float plate glass, polished plate glass, figured glass, wired glass, colored plate glass, heat-absorbing glass, heat-reflecting glass, and green glass. Organic plastic plates such as polycarbonate and polyacrylate may also be exemplified.

Two kinds or more of plate glasses may be used as the glass plate. For example, a laminated glass in which the interlayer film for a laminated glass of the present invention is sandwiched between a transparent float glass plate and a colored glass plate such as a green glass may be exemplified.

When the laminated glass is used as glass for vehicles, it may be used as a windshield, a side glass, a rear glass, a roof glass, or a panorama glass.

Furthermore, a production method of the laminated glass is not particularly limited, and a conventionally method can be used.

When the interlayer film for a laminated glass of the present invention is used in the laminated glass, the laminated glass shows a sufficiently low transmittance of ultraviolet rays having wavelength of 380 to 400 nm while maintaining high visible right transmittance. Moreover, the laminated glass can maintain ultraviolet blocking properties for a long time, and the hue thereof hardly changes even under exposure to sunlight.

Effects of the Invention

The present invention can provide an interlayer film for a laminated glass which can reduce transmittance of ultraviolet rays having wavelength of 380 to 400 nm and has excellent durability to light exposure while maintaining high visible light transmittance.

BEST MODE FOR CARRYING OUT THE INVENTION

The following description will discuss details of embodiments of the present invention by showing Examples, but the present invention is not limited to those Examples.
(Preparation of Indole Compound)
(1) Preparation of Indole Compound A To 120 ml of methanol were added 23.5 g (0.10 mol) of 1-methyl-2-phenyl-1H-indole-3-carbaldehyde and 11.9 g (0.12 mol) of methyl cyanoacetate to produce a mixture. Subsequently, 2.5 g (0.03 mol) of piperidine was added to the mixture, reacted under reflux for 6 hours, and cooled to room temperature to precipitate a crystal. The obtained crystal was washed with a small amount of methanol, and then dried to give 30.9 g of a light-yellow crystalline indole compound A having a structure of the general Chemical Formula (1) in which $R^1$ was methyl group and $R^2$ was methyl group. The melting point of the obtained indole compound A was 193.7° C.

(2) Preparation of Indole Compound B

An amount of 28.9 g of a light-yellow crystalline indole compound B having a structure of the general Chemical Formula (1) in which $R^1$ was ethyl group and $R^2$ was methyl group was obtained by the same method as the preparation method of the indole compound A, except that ethanol was used instead of methanol and ethyl cyanoacetate (0.12 mol) was used instead of methyl cyanoacetate. The melting point of the obtained indole compound B was 145° C.

(3) Preparation of Indole Compound C

An amount of 32.7 g of a light-yellow crystalline indole compound C having a structure of the general Chemical Formula (1) in which $R^1$ was isopropyl group and $R^2$ was methyl group was obtained by the same method as the preparation method of the indole compound A, except that isopropyl alcohol was used instead of methanol and isopropyl cyanoacetate (0.12 mol) was used instead of methyl cyanoacetate. The melting point of the obtained indole compound C was 170.1° C.

(4) Preparation of Indole Compound D

An amount of 33.7 g of a light-yellow crystalline indole compound D having a structure of the general Chemical Formula (1) in which $R^1$ was butyl group and $R^2$ was methyl group was obtained by the same method as the preparation method of the indole compound A, except that butanol was used instead of methanol and butyl cyanoacetate (0.12 mol) was used instead of methyl cyanoacetate. The melting point of the obtained indole compound D was 126° C.

(5) Preparation of Indole Compound E

An amount of 35.0 g of a light-yellow crystalline indole compound E having a structure of the general Chemical Formula (1) in which $R^1$ was pentyl group and $R^2$ was methyl group was obtained by the same method as the preparation method of the indole compound A, except that pentanol was used instead of methanol and pentyl cyanoacetate (0.12 mol) was used instead of methyl cyanoacetate.

(6) Preparation of Indole Compound F

An amount of 28.4 g of a light-yellow crystalline indole compound F having a structure of the general Chemical Formula (1) in which $R^1$ was methyl group and $R^2$ was hydrogen was obtained by the same method as the preparation method of the indole compound A, except that 2-phenyl-1H-indole-3-carbaldehyde (0.10 mol) was used instead of 1-methyl-2-phenyl-1H-indole-3-carbaldehyde.

(7) Preparation of Indole Compound G

An amount of 31.1 g of a light-yellow crystalline indole compound G having a structure of the general Chemical Formula (1) in which $R^1$ was methyl group and $R^2$ was ethyl group was obtained by the same method as the preparation method of the indole compound A, except that 1-ethyl-2-phenyl-1H-indole-3-carbaldehyde (0.10 mol) was used instead of 1-methyl-2-phenyl-1H-indole-3-carbaldehyde.

(8) Preparation of Indole Compound H

An amount of 33.7 g of a light-yellow crystalline indole compound H having a structure of the general Chemical Formula (1) in which $R^1$ was methyl group and $R^2$ was butyl group was obtained by the same method as the preparation method of the indole compound A, except that 1-butyl-2-phenyl-1H-indole-3-carbaldehyde (0.10 mol) was used instead of 1-methyl-2-phenyl-1H-indole-3-carbaldehyde.

(9) Preparation of Indole Compound I

An amount of 36.3 g of a light-yellow crystalline indole compound I having a structure of the general Chemical Formula (1) in which $R^1$ was methyl group and $R^2$ was —$CH_2$—$CH(C_2H_5)$—$C_4H_9$ group was obtained by the same method as the preparation method of the indole compound A, except that 1-(2-ethyl-hexyl)-2-phenyl-1H-indole-3-carbaldehyde (0.10 mol) was used instead of 1-methyl-2-phenyl-1H-indole-3-carbaldehyde.

(10) Preparation of Indole Compound J

An amount of 36.9 g of a light-yellow crystalline indole compound J having a structure of the general Chemical Formula (1) in which $R^1$ was methyl group and $R^2$ was —$CH_2Ph$ group was obtained by the same method as the preparation method of the indole compound A, except that 1-benzyl-2-phenyl-1H-indole-3-carbaldehyde (0.10 mol) was used instead of 1-methyl-2-phenyl-1H-indole-3-carbaldehyde.

(11) Preparation of Indole Compound K

An amount of 32.4 g of a light-yellow crystalline indole compound K having a structure of the general Chemical Formula (1) in which $R^1$ was butyl group and $R^2$ was hydrogen was obtained by the same method as the preparation method of the indole compound D, except that 2-phenyl-1H-indole-3-carbaldehyde (0.10 mol) was used instead of 1-methyl-2-phenyl-1H-indole-3-carbaldehyde.

(12) Preparation of Indole Compound L

An amount of 35.0 g of a light-yellow crystalline indole compound L having a structure of the general Chemical Formula (1) in which $R^1$ was butyl group and $R^2$ was ethyl group was obtained by the same method as the preparation method of the indole compound D, except that 1-ethyl-2-phenyl-1H-indole-3-carbaldehyde (0.10 mol) was used instead of 1-methyl-2-phenyl-1H-indole-3-carbaldehyde.

(13) Preparation of Indole Compound M

An amount of 37.6 g of a light-yellow crystalline indole compound M having a structure of the general Chemical Formula (1) in which $R^1$ was butyl group and $R^2$ was butyl group was obtained by the same method as the preparation method of the indole compound D, except that 1-butyl-2-phenyl-1H-indole-3-carbaldehyde (0.10 mol) was used instead of 1-methyl-2-phenyl-1H-indole-3-carbaldehyde.

(14) Preparation of Indole Compound N

An amount of 40.2 g of a light-yellow crystalline indole compound N having a structure of the general Chemical Formula (1) in which $R^1$ was butyl group and $R^2$ was —$CH_2$—$CH(C_2H_5)$—$C_4H_9$ group was obtained by the same method as the preparation method of the indole compound D, except that 1-(2-ethyl-hexyl)-2-phenyl-1H-indole-3-carbaldehyde (0.10 mol) was used instead of 1-methyl-2-phenyl-1H-indole-3-carbaldehyde.

(15) Preparation of Indole Compound O

An amount of 40.8 g of a light-yellow crystalline indole compound O having a structure of the general Chemical Formula (1) in which $R^1$ was butyl group and $R^2$ was —$CH_2$Ph group was obtained by the same method as the preparation method of the indole compound D, except that 1-benzyl-2-phenyl-1H-indole-3-carbaldehyde (0.10 mol) was used instead of 1-methyl-2-phenyl-1H-indole-3-carbaldehyde.

(16) Preparation of Indole Compound P

An amount of 29.1 g of a light-yellow crystalline indole compound P having a structure of the general Chemical Formula (1) in which $R^1$ was hydrogen and $R^2$ was methyl group was obtained by the same method as the preparation method of the indole compound A, except that toluene was used instead of methanol and cyanoacetic acid (0.12 mol) was used instead of methyl cyanoacetate. The melting point of the obtained indole compound P was 203.5° C.

(17) Preparation of Indole Compound Q

To 200 ml of N,N-dimethylformamide (DMF) were added 30.0 g (0.10 mol) of the indole compound P and 14.4 g of anhydrous potassium carbonate to produce a mixture. Subsequently, 25.6 g (0.20 mol) of 2-bromoethanol was added to the mixture to give a liquid mixture. The obtained liquid mixture was reacted at 70° C. for 6 hours, and then cooled to room temperature. Thereafter, 1000 ml of water and 500 ml of ethyl acetate were added to the reaction mixture, and the organic layer was washed with 1000 ml of water three times. Hexane was added to the organic layer to precipitate a crystal. The obtained crystal was dried to give 19.1 g of a light-yellow crystalline indole compound Q having a structure of the general Chemical Formula (1) in which $R^1$ was —$C_2H_4$OH group and $R^2$ was methyl group. The melting point of the obtained indole compound Q was 145.6° C.

(18) Preparation of Indole Compound R

An amount of 29.9 g of a light-yellow crystalline indole compound R having a structure represented by the following Chemical Formula (2) was obtained by the same method as the preparation method of the indole compound A, except that ethanol was used instead of methanol, phenylacetonitrile (0.12 mol) was used instead of methyl cyanoacetate, and 48% solution of potassium hydroxide (0.30 mol) was used instead of piperidine. The melting point of the obtained indole compound R was 183.7° C.

[Chemical Formula 2]

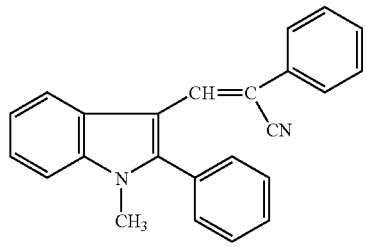

(2)

(19) Preparation of Indole Compound S

An amount of 27.5 g of a light-yellow crystalline indole compound S having a structure represented by the following Chemical Formula (3) was obtained by the same method as the preparation method of the indole compound A, except that ethanol was used instead of methanol, malononitrile (0.12 mol) was used instead of methyl cyanoacetate, and triethylamine (0.03 mol) was used instead of piperidine. The melting point of the obtained indole compound S was 203.2° C.

[Chemical Formula 3]

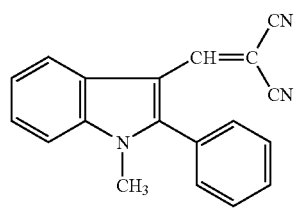

(3)

(20) Preparation of Indole Compound T

An amount of 31.75 g of a light-yellow crystalline indole compound T having a structure of the general Chemical Formula (1) in which $R^1$ was —$C_2H_4OC_2H_5$ group and $R^2$ was methyl group was obtained by the same method as the preparation method of the indole compound A, except that 2-ethoxyethanol was used instead of methanol and 2-ethoxyethyl cyanoacetate (0.12 mol) was used instead of methyl cyanoacetate. The melting point of the obtained indole compound T was 127.3° C.

Table 1 shows the structure of the prepared indole compounds. It is to be noted that BONASORB UA3901 (produced by Orient Chemical industries, Ltd.) is an indole compound.

TABLE 1

| Indole compound | $R^1$ | $R^2$ | Relationship with Chemical Formula (1) |
|---|---|---|---|
| A | —CH₃ | —CH₃ | Compatible |
| B | —C₂H₅ | —CH₃ | Compatible |
| C | —C₃H₇ | —CH₃ | Compatible |
| D | —C₄H₉ | —CH₃ | Incompatible |
| E | —C₅H₁₁ | —CH₃ | Incompatible |
| F | —CH₃ | —H | Compatible |
| G | —CH₃ | —C₂H₅ | Compatible |
| H | —CH₃ | —C₄H₉ | Compatible |
| I | —CH₃ | —CH₂—CH(C₂H₅)—C₄H₉ | Compatible |
| J | —CH₃ | —CH₂—Ph | Compatible |
| K | —C₄H₉ | —H | Incompatible |
| L | —C₄H₉ | —C₂H₅ | Incompatible |
| M | —C₄H₉ | —C₄H₉ | Incompatible |
| N | —C₄H₉ | —CH₂—CH(C₂H₅)—C₄H₉ | Incompatible |
| O | —C₄H₉ | —CH₂—Ph | Incompatible |
| P | —H | —CH₃ | Incompatible |
| Q | —C₂H₄OH | —CH₃ | Incompatible |
| R | Chemical Formula (2) | | Incompatible |
| S | Chemical Formula (3) | | Incompatible |
| T | —C₂H₄OC₂H₅ | —CH₃ | Incompatible |
| BONASORB UA3901 | — | | Incompatible |

Example 1

(1) Production of Interlayer Film for Laminated Glass

To 40 parts by weight of triethylene glycol di-2-ethylhexanoate (3GO) as a plasticizer were added 0.4 parts by weight of 2,6-di-t-butyl-p-cresol (BHT) as an antioxidant, 0.4 parts by weight of an ultraviolet absorber ("TINUVIN 326" produced by Ciba Specialty Chemicals Inc.) having a benzotriazol structure, and 0.048 parts by weight of the obtained indole compound A. The resultant mixture was stirred by using a stirrer at 80° C. for 30 minutes to give a plasticizer solution.

The obtained plasticizer solution was sufficiently mixed with 100 parts by weight of polyvinyl butyral resin (PVB) (average polymerization degree: 1700, butyralation degree: 68.5 mol %, amount of the hydroxyl group: 30.6 mol %, amount of the acetyl group: 0.9 mol %). Then, a twin-screw aeolotropic extruder was used to produce an interlayer film for a laminated glass having a film thickness of 760 μm. In this process, for the purpose of controlling the adhesion of the interlayer film for a laminated glass, a magnesium acetate solution was added so that concentration of Mg in the interlayer film for a laminated glass was 65 ppm.

(2) Production of Laminated Glass

The obtained interlayer film for a laminated glass was put for 24 hours under the constant temperature and humidity conditions, at a temperature of 23° C. and a relative humidity of 28%, and thereafter sandwiched between two sheets of transparent float glass (clear glass: 300 mm in length×300 mm in width×2.5 mm in thickness) to form a laminated body. The obtained laminated body was temporarily-press-bonded by using a roller heated at 230° C. The temporarily-press-bonded laminated glass was press-bonded using an autoclave, for 20 minutes at a temperature of 135° C. and a pressure of 1.2 MPa, to produce a laminated glass. Similarly, another laminated glass was produced by using float glass (clear glass) with 500 mm in length×500 mm in width×2.5 mm in thickness.

Examples 2 to 27, and Comparative Examples 1 to 15

Interlayer films for a laminated glass and laminated glasses were produced in the same manner as in Example 1, except that the compositions thereof were changed as shown in Tables 2 to 6. Meanwhile, interlayer films for a laminated glass and laminated glasses were produced in Examples 4, 8, and 12 in the same manner as in Example 1, except that 0.28 parts by weight of tin-doped indium oxide particles (ITO) (volume average particle diameter: 35 nm) were added to the plasticizer solution as an infrared absorber.

(Evaluations)

The following evaluations were made for each of the laminated glasses obtained in Examples and Comparative Examples.

Tables 2 to 6 show the results.

(1) Evaluation of Transmittance

The visible light transmittance (Tv) of the obtained laminated glass (300 mm in length×300 mm in width) was calculated according to JIS R 3106 (1998) by using a spectrophotometer ("U-4000" produced by Hitachi, Ltd.). The solar transmittance (Ts) of the obtained laminated glass was also determined at wavelength of 300 to 2500 nm.

Using the spectrophotometer ("U-4000" produced by a Hitachi, Ltd.), the transmittances of the laminated glass at wavelength of 380 nm, 390 nm, and 400 nm were measured respectively to find an average value T of the transmittance (380 to 400 nm). The average value T of the transmittance (380 to 400 nm) was determined for the laminated glass before and after the light exposure test (2) to be mentioned later.

(2) Light Exposure Test

The obtained laminated glass was exposed with ultraviolet rays for 2000 hours using an ultraviolet irradiation apparatus according to JIS R 3205 (1998), and the change in hue was evaluated with the color difference ΔE before and after ultraviolet irradiation.

(3) Evaluation of Preventive Effect on Pest Insect Attraction

A transparent adhesive was applied to the glass surface of one side of the obtained laminated glass (500 mm in length× 500 mm in width). A halogen lamp is provided on the glass side to which the transparent adhesive is not applied, and the laminated glass was left to stand outdoors (Sekisui Chemical's Shiga Minakuchi Plant, in August, 2008) for 1 hour (from 20:00 to 21:00) with the white light of the halogen lamp on. The number of winged insects that had been captured to the transparent adhesive after being left standing was calculated.

(4) Evaluation of Penetration Resistance

The obtained laminated glass (300 mm in length×300 mm in width) was adjusted so as to have a surface temperature of 23° C. Subsequently, according to JIS R 3212, a rigid sphere having a mass of 2260 g and a diameter of 82 mm was dropped from a height of 4 m to the central point of the laminated glass. The same test was made for in total six sheets of laminated glasses. The test result was expressed as "pass" in the case where a rigid sphere did not penetrate through the laminated glass within 5 seconds after the impact of the rigid sphere on the laminated glass for all the six sheets of the laminated glass. Also, the test result was expressed as "fail" in the case where the number of sheets of the laminated glass through which a rigid sphere did not penetrate within 5 seconds after the impact of the rigid sphere was less than or equal to three. In the case where the number of sheets of the laminated glass through which a rigid sphere did not penetrate within 5 seconds after the impact of the rigid sphere was four, a retest was made for another six sheets of the laminated glass. In the case where the number of sheets of the laminated glass through which a rigid sphere did not penetrate within 5 seconds after the impact of the rigid sphere was five, one more sheet of the laminated glass was additionally tested; and the test result was evaluated as "pass" in the case where a rigid sphere did not penetrate through the laminated glass within 5 seconds after impact of the rigid sphere.

The same evaluations of penetration resistance were performed for the fall heights of 5 m and 6 m, respectively, in addition to the test for the fall heights of 4 m.

(5) Durability Test to Heat

The obtained laminated glass (300 mm in length×300 mm in width) was vertically set under a constant temperature at 100° C. for one month. The change in hue was evaluated based on the color difference ΔE before and after the test.

The number of bubble generated after the test was counted. With regard to bubble's size, bubbles were classified into three:
1. The length of its longest side is less than 5 mm
2. The length of its longest side is greater than or equal to 5 mm, and less than 10 mm
3. The length of its longest side is greater than or equal to 10 mm.

Then, the numbers of bubble for each classification were counted.

(6) Observation of Solid Components

The interlayer film specimen having a size of 300 mm in length×300 mm in width was cut from the produced interlayer film and wrapped with an aluminum bag. The wrapped sample was kept for one month at a constant temperature of 5° C. Then, the interlayer film was observed with the naked eye, and it was checked whether there are any solid components or not. The solid components are presumably either an indole compound or an ultraviolet absorber having a benzotriazol structure.

TABLE 2

| | | | Example | | | | | | | | | |
|---|---|---|---|---|---|---|---|---|---|---|---|---|
| | | | 1 | 2 | 3 | 4 | 5 | 6 | 7 | 8 | 9 | 10 |
| Composition (parts by weight) | PVB | | 100 | 100 | 100 | 100 | 100 | 100 | 100 | 100 | 100 | 100 |
| | Plasticizer (3GO) | | 40 | 40 | 40 | 40 | 40 | 40 | 40 | 40 | 40 | 40 |
| | Indole compound | A | 0.048 | 0.14 | 0.2 | 0.14 | — | — | — | — | — | — |
| | | B | — | — | — | — | 0.048 | 0.14 | 0.2 | 0.14 | — | — |
| | | C | — | — | — | — | — | — | — | — | 0.048 | 0.14 |
| | | D | — | — | — | — | — | — | — | — | — | — |
| | | E | — | — | — | — | — | — | — | — | — | — |
| | Antioxidant | | 0.4 | 0.4 | 0.4 | 0.4 | 0.4 | 0.4 | 0.4 | 0.4 | 0.4 | 0.4 |
| | Ultraviolet absorber | | 0.4 | 0.4 | 0.4 | 0.4 | 0.4 | 0.4 | 0.4 | 0.4 | 0.4 | 0.4 |
| | ITO | | 0 | 0 | 0 | 0.28 | 0 | 0 | 0 | 0.28 | 0 | 0 |
| | Mg/ppm | | 65 | 65 | 65 | 65 | 65 | 65 | 65 | 65 | 65 | 65 |
| | Concentration of light absorber/weight % | | 0.034 | 0.099 | 0.142 | 0.099 | 0.034 | 0.099 | 0.142 | 0.099 | 0.034 | 0.099 |
| Evaluation of transmittance | Transmittance/% | Ts | 79.0 | 78.8 | 78.7 | 65.6 | 79.1 | 78.8 | 78.2 | 65.9 | 78.5 | 78.9 |
| | | Tv | 88.3 | 88.6 | 88.4 | 87.4 | 88.2 | 88.5 | 88.4 | 87.1 | 88.4 | 88.3 |
| | T(380-400 nm)/% | Before ultraviolet irradiation | 0.35 | 0.04 | 0.02 | 0.04 | 0.46 | 0.05 | 0.02 | 0.03 | 0.51 | 0.08 |
| | | After ultraviolet irradiation | 0.40 | 0.16 | 0.10 | 0.18 | 0.50 | 0.26 | 0.13 | 0.18 | 0.57 | 0.30 |
| Light exposure test | ΔE | | 1.07 | 1.14 | 1.30 | 1.21 | 1.06 | 1.22 | 1.41 | 1.50 | 1.19 | 1.44 |
| Evaluation of preventive effect on pest insect attraction | The number of attracted winged insects | | 7 | 3 | 5 | 5 | 8 | 2 | 6 | 4 | 8 | 3 |
| Evaluation of penetration resistance | 4 m | | Pass | Pass | Pass | Pass | Pass | Pass | Pass | Pass | Pass | Pass |
| | 5 m | | Pass | Pass | Pass | Pass | Pass | Pass | Pass | Pass | Pass | Pass |
| | 6 m | | Pass | Pass | Pass | Pass | Pass | Pass | Pass | Pass | Pass | Pass |
| Durability test to heat | ΔE | | 0.26 | 0.38 | 0.55 | 0.46 | 0.30 | 0.39 | 0.54 | 0.50 | 0.31 | 0.42 |
| | The number of bubble less than 5 mm | | 0 | 0 | 0 | 0 | 0 | 0 | 0 | 0 | 0 | 0 |
| | The number of bubble greater than or equal to 5 mm, and less than 10 mm | | 0 | 0 | 0 | 0 | 0 | 0 | 0 | 0 | 0 | 0 |
| | The number of bubble greater than or equal to 10 mm | | 0 | 0 | 0 | 0 | 0 | 0 | 0 | 0 | 0 | 0 |
| | Presence of solid components | | Absent | Absent | Absent | Absent | Absent | Absent | Absent | Absent | Absent | Absent |

TABLE 3

| | | | Example | | Comparative Example | | | |
|---|---|---|---|---|---|---|---|---|
| | | | 11 | 12 | 1 | 2 | 3 | 4 |
| Composition (parts by weight) | PVB | | 100 | 100 | 100 | 100 | 100 | 100 |
| | Plasticizer (3GO) | | 40 | 40 | 40 | 40 | 40 | 40 |
| | Indole compound | A | — | — | — | — | — | — |
| | | B | — | — | — | — | — | — |
| | | C | 0.2 | 0.14 | — | — | — | — |
| | | D | — | — | 0.14 | — | — | — |
| | | E | — | — | — | 0.14 | — | — |
| | Antioxidant | | 0.4 | 0.4 | 0.4 | 0.4 | 0.4 | 0.4 |
| | Ultraviolet absorber | | 0.4 | 0.4 | 0.4 | 0.4 | 0.4 | 0.8 |
| | ITO | | 0 | 0.28 | 0 | 0 | 0 | 0 |
| | Mg/ppm | | 65 | 65 | 65 | 65 | 65 | 65 |
| | Concentration of light absorber/weight % | | 0.142 | 0.099 | 0.099 | 0.099 | 0.000 | 0.000 |
| Evaluation of transmittance | Transmittance/% | Ts | 78.2 | 67.3 | 78.6 | 78.5 | 79.1 | 78.9 |
| | | Tv | 88.3 | 87.2 | 88.5 | 88.3 | 88.6 | 88.1 |
| | T(380-400 nm)/% | Before ultraviolet irradiation | 0.03 | 0.08 | 0.06 | 0.05 | 10.25 | 2.49 |
| | | After ultraviolet irradiation | 0.14 | 0.30 | 0.66 | 0.84 | 10.17 | 2.51 |

TABLE 3-continued

|  |  | Example | | Comparative Example | | | |
|---|---|---|---|---|---|---|---|
|  |  | 11 | 12 | 1 | 2 | 3 | 4 |
| Light exposure test | ΔE | 1.65 | 1.48 | 3.01 | 3.96 | 0.30 | 0.25 |
| Evaluation of preventive effect on pest insect attraction | The number of attracted winged insects | 6 | 4 | 3 | 5 | 27 | 19 |
| Evaluation of penetration resistance | 4 m | Pass | Pass | Pass | Pass | Pass | Pass |
|  | 5 m | Pass | Pass | Pass | Pass | Pass | Pass |
|  | 6 m | Pass | Pass | Pass | Pass | Pass | Pass |
| Durability test to heat | ΔE | 0.63 | 0.59 | 2.17 | 2.33 | 0.15 | 0.13 |
|  | The number of bubble less than 5 mm | 0 | 0 | 0 | 0 | 0 | 0 |
|  | The number of bubble greater than or equal to 5 mm, and less than 10 mm | 0 | 0 | 0 | 0 | 0 | 0 |
|  | The number of bubble greater than or equal to 10 mm | 0 | 0 | 0 | 0 | 0 | 0 |
|  | Presence of solid components | Absent | Absent | Absent | Absent | Absent | Absent |

TABLE 4

|  |  |  | Example | | | | | | | |
|---|---|---|---|---|---|---|---|---|---|---|
|  |  |  | 13 | 14 | 15 | 16 | 17 | 18 | 19 | 20 |
| Composition (parts by weight) | PVB | | 100 | 100 | 100 | 100 | 100 | 100 | 100 | 100 |
|  | Plasticizer (3GO) | | 40 | 40 | 40 | 40 | 40 | 40 | 40 | 40 |
|  | Indole compound | F | 0.14 | 0.048 | 0.2 | — | — | — | — | — |
|  |  | G | — | — | — | 0.14 | 0.048 | 0.2 | — | — |
|  |  | H | — | — | — | — | — | — | 0.14 | 0.048 |
|  |  | I | — | — | — | — | — | — | — | — |
|  |  | J | — | — | — | — | — | — | — | — |
|  | Antioxidant | | 0.4 | 0.4 | 0.4 | 0.4 | 0.4 | 0.4 | 0.4 | 0.4 |
|  | Ultraviolet absorber | | 0.4 | 0.4 | 0.4 | 0.4 | 0.4 | 0.4 | 0.4 | 0.4 |
|  | ITO | | 0 | 0 | 0 | 0 | 0 | 0 | 0 | 0 |
|  | Mg/ppm | | 65 | 65 | 65 | 65 | 65 | 65 | 65 | 65 |
|  | Concentration of light absorber/weight % | | 0.099 | 0.034 | 0.142 | 0.099 | 0.034 | 0.142 | 0.099 | 0.034 |
| Evaluation of transmittance | Transmittance/% | Ts | 78.5 | 78.8 | 78.9 | 78.3 | 78.1 | 78.3 | 78.9 | 78.8 |
|  |  | Tv | 88.4 | 88.8 | 88.5 | 88.2 | 89.0 | 89.2 | 88.4 | 88.6 |
|  | T(380-400 nm)/% | Before ultraviolet irradiation | 0.08 | 0.46 | 0.02 | 0.04 | 0.52 | 0.03 | 0.07 | 0.44 |
|  |  | After ultraviolet irradiation | 0.19 | 0.68 | 0.11 | 0.16 | 0.74 | 0.13 | 0.18 | 0.60 |
| Light exposure test | ΔE | | 1.18 | 0.95 | 1.31 | 1.28 | 1.18 | 1.46 | 1.20 | 0.87 |
| Evaluation of preventive effect on pest insect attraction | The number of attracted winged insects | | 4 | 4 | 8 | 5 | 3 | 6 | 8 | 5 |
| Evaluation of penetration resistance | 4 m | | Pass | Pass | Pass | Pass | Pass | Pass | Pass | Pass |
|  | 5 m | | Pass | Pass | Pass | Pass | Pass | Pass | Pass | Pass |
|  | 6 m | | Pass | Pass | Pass | Pass | Pass | Pass | Pass | Pass |
| Durability test to heat | ΔE | | 0.44 | 0.27 | 0.61 | 0.38 | 0.17 | 0.50 | 0.35 | 0.22 |
|  | The number of bubble less than 5 mm | | 0 | 0 | 0 | 0 | 0 | 0 | 0 | 0 |
|  | The number of bubble greater than or equal to 5 mm, and less than 10 mm | | 0 | 0 | 0 | 0 | 0 | 0 | 0 | 0 |
|  | The number of bubble greater than or equal to 10 mm | | 0 | 0 | 0 | 0 | 0 | 0 | 0 | 0 |
|  | Presence of solid components | | Absent | Absent | Absent | Absent | Absent | Absent | Absent | Absent |

|  |  |  | Example | | | | | | |
|---|---|---|---|---|---|---|---|---|---|
|  |  |  | 21 | 22 | 23 | 24 | 25 | 26 | 27 |
| Composition (parts by weight) | PVB | | 100 | 100 | 100 | 100 | 100 | 100 | 100 |
|  | Plasticizer (3GO) | | 40 | 40 | 40 | 40 | 40 | 40 | 40 |
|  | Indole compound | F | — | — | — | — | — | — | — |
|  |  | G | — | — | — | — | — | — | — |
|  |  | H | 0.2 | — | — | — | — | — | — |
|  |  | I | — | 0.14 | 0.048 | 0.2 | — | — | — |
|  |  | J | — | — | — | — | 0.14 | 0.048 | 0.2 |
|  | Antioxidant | | 0.4 | 0.4 | 0.4 | 0.4 | 0.4 | 0.4 | 0.4 |
|  | Ultraviolet absorber | | 0.4 | 0.4 | 0.4 | 0.4 | 0.4 | 0.4 | 0.4 |
|  | ITO | | 0 | 0 | 0 | 0 | 0 | 0 | 0 |
|  | Mg/ppm | | 65 | 65 | 65 | 65 | 65 | 65 | 65 |
|  | Concentration of light absorber/weight % | | 0.142 | 0.099 | 0.034 | 0.142 | 0.099 | 0.034 | 0.142 |
| Evaluation of transmittance | Transmittance/% | Ts | 78.5 | 78.4 | 78.9 | 78.4 | 78.6 | 78.3 | 78.8 |
|  |  | Tv | 88.1 | 88.3 | 89.0 | 88.4 | 88.2 | 88.6 | 88.6 |
|  | T(380-400 nm)/% | Before ultraviolet irradiation | 0.02 | 0.06 | 0.59 | 0.04 | 0.05 | 0.47 | 0.01 |
|  |  | After ultraviolet irradiation | 0.09 | 0.21 | 0.81 | 0.18 | 0.18 | 0.78 | 0.10 |

TABLE 4-continued

|  |  |  |  |  |  |  |  |
|---|---|---|---|---|---|---|---|
| Light exposure test | ΔE | 1.29 | 1.17 | 0.88 | 1.58 | 1.26 | 1.04 | 1.55 |
| Evaluation of preventive effect on pest insect attraction | The number of attracted winged insects | 2 | 3 | 6 | 4 | 7 | 5 | 2 |
| Evaluation of penetration resistance | 4 m | Pass | Pass | Pass | Pass | Pass | Pass | Pass |
|  | 5 m | Pass | Pass | Pass | Pass | Pass | Pass | Pass |
|  | 6 m | Pass | Pass | Pass | Pass | Pass | Pass | Pass |
| Durability test to heat | ΔE | 0.77 | 0.29 | 0.20 | 0.31 | 0.46 | 0.28 | 0.58 |
|  | The number of bubble less than 5 mm | 0 | 0 | 0 | 0 | 0 | 0 | 0 |
|  | The number of bubble greater than or equal to 5 mm, and less than 10 mm | 0 | 0 | 0 | 0 | 0 | 0 | 0 |
|  | The number of bubble greater than or equal to 10 mm | 0 | 0 | 0 | 0 | 0 | 0 | 0 |
|  | Presence of solid components | Absent | Absent | Absent | Absent | Absent | Absent | Absent |

TABLE 5

|  |  |  | Comparative Example | | | | |
|---|---|---|---|---|---|---|---|
|  |  |  | 5 | 6 | 7 | 8 | 9 |
| Composition (parts by weight) | PVB | | 100 | 100 | 100 | 100 | 100 |
|  | Plasticizer (3GO) | | 40 | 40 | 40 | 40 | 40 |
|  | Indole compound | K | 0.14 | — | — | — | — |
|  |  | L | — | 0.14 | — | — | — |
|  |  | M | — | — | 0.14 | — | — |
|  |  | N | — | — | — | 0.14 | — |
|  |  | O | — | — | — | — | 0.14 |
|  | Antioxidant | | 0.4 | 0.4 | 0.4 | 0.4 | 0.4 |
|  | Ultraviolet absorber | | 0.4 | 0.4 | 0.4 | 0.4 | 0.4 |
|  | ITO | | 0 | 0 | 0 | 0 | 0 |
|  | Mg/ppm | | 65 | 65 | 65 | 65 | 65 |
|  | Concentration of light absorber/weight % | | 0.099 | 0.099 | 0.099 | 0.099 | 0.099 |
| Evaluation of transmittance | Transmittance (%) | Ts | 78.8 | 78.4 | 78.6 | 78.8 | 78.4 |
|  |  | Tv | 88.4 | 88.4 | 88.5 | 88.3 | 88.2 |
|  | T(380-400 nm) | Before ultraviolet irradiation | 0.07 | 0.06 | 0.08 | 0.05 | 0.05 |
|  |  | After ultraviolet irradiation | 0.82 | 0.75 | 0.88 | 0.76 | 0.92 |
| Light exposure test | ΔE | | 3.33 | 3.26 | 3.10 | 3.81 | 3.45 |
| Evaluation of preventive effect on pest insect attraction | The number of attracted winged insects | | 5 | 4 | 6 | 8 | 2 |
| Evaluation of penetration resistance | 4 m | | Pass | Pass | Pass | Pass | Pass |
|  | 5 m | | Pass | Pass | Pass | Pass | Pass |
|  | 6 m | | Pass | Pass | Pass | Pass | Pass |
| Durability test to heat | ΔE | | 1.96 | 2.08 | 1.85 | 2.17 | 1.58 |
|  | The number of bubble less than 5 mm | | 0 | 0 | 0 | 0 | 0 |
|  | The number of bubble greater than or equal to 5 mm, and less than 10 mm | | 0 | 0 | 0 | 0 | 0 |
|  | The number of bubble greater than or equal to 10 mm | | 0 | 0 | 0 | 0 | 0 |
|  | Presence of solid components | | Absent | Absent | Absent | Absent | Absent |

TABLE 6

|  |  |  | Comparative Example | | | | | |
|---|---|---|---|---|---|---|---|---|
|  |  |  | 10 | 11 | 12 | 13 | 14 | 15 |
| Composition (parts by weight) | PVB | | 100 | 100 | 100 | 100 | 100 | 100 |
|  | Plasticizer (3GO) | | 40 | 40 | 40 | 40 | 40 | 40 |
|  | Indole compound | P | 0.14 | — | — | — | — | — |
|  |  | Q | — | 0.14 | — | — | — | — |
|  |  | R | — | — | 0.14 | — | — | — |
|  |  | S | — | — | — | 0.14 | — | — |
|  |  | T | — | — | — | — | — | 0.14 |
|  | BONASORB UA3901 | | — | — | — | — | 0.14 | — |
|  | Antioxidant | | 0.4 | 0.4 | 0.4 | 0.4 | 0.4 | 0.4 |
|  | Ultraviolet absorber | | 0.4 | 0.4 | 0.4 | 0.4 | 0.4 | 0.4 |
|  | ITO | | 0 | 0 | 0 | 0 | 0 | 0 |
|  | Mg/ppm | | 65 | 65 | 65 | 65 | 65 | 65 |
|  | Concentration of light absorber/weight % | | 0.099 | 0.099 | 0.099 | 0.099 | 0.099 | 0.099 |
| Evaluation of transmittance | Transmittance/% | Ts | 79.0 | 79.1 | 78.4 | 78.1 | 78.4 | 78.7 |
|  |  | Tv | 88.1 | 88.6 | 88.2 | 87.6 | 88.3 | 88.5 |
|  | T(380-400 nm)/% | Before ultraviolet irradiation | 0.30 | 0.07 | 0.34 | 0.03 | 0.05 | 0.09 |
|  |  | After ultraviolet irradiation | 1.06 | 0.58 | 1.09 | 0.67 | 0.64 | 0.52 |

TABLE 6-continued

|  |  | Comparative Example | | | | | |
|---|---|---|---|---|---|---|---|
|  |  | 10 | 11 | 12 | 13 | 14 | 15 |
| Light exposure test | ΔE | 2.73 | 3.06 | 4.13 | 3.65 | 3.68 | 2.87 |
| Evaluation of preventive effect on pest insect attraction | The number of attracted winged insects | 3 | 2 | 4 | 6 | 3 | 4 |
| Evaluation of penetration resistance | 4 m | Pass | Pass | Pass | Pass | Pass | Pass |
|  | 5 m | Fail | Fail | Pass | Pass | Pass | Pass |
|  | 6 m | Fail | Fail | Pass | Pass | Pass | Pass |
| Durability test to heat | ΔE | 1.90 | 2.34 | 3.71 | 3.07 | 3.22 | 1.99 |
|  | The number of bubble less than 5 mm | 0 | 0 | 0 | 0 | 0 | 0 |
|  | The number of bubble greater than or equal to 5 mm, and less than 10 mm | 0 | 0 | 0 | 0 | 0 | 0 |
|  | The number of bubble greater than or equal to 10 mm | 0 | 0 | 0 | 0 | 0 | 0 |
|  | Presence of solid components | Present | Present | Absent | Absent | Absent | Absent |

Example 28

(1) Production of Interlayer Film for Laminated Glass

To 63 parts by weight of tetraethylene glycol-di-2-ethyl-hexanoate (4GO) as a plasticizer were added 0.4 parts by weight of 2,6-di-t-butyl-p-cresol as an antioxidant, 0.4 parts by weight of an ultraviolet absorber ("TINUVIN 326" produced by Ciba Specialty Chemicals Inc.) having a benzotriazol structure, and 0.14 parts by weight of the obtained indole compound A. The resultant mixture was stirred by using a stirrer at 80° C. for 30 minutes to give a plasticizer solution.

The obtained plasticizer solution was sufficiently mixed with 100 parts by weight of polyvinyl butyral resin (PVB) (average polymerization degree: 1700, butyralation degree: 68.5 mol %, amount of the hydroxyl group: 30.6 mol %, amount of the acetyl group: 0.9 mol %). Then, a twin-screw aeolotropic extruder was used to produce an interlayer film for a laminated glass having a film thickness of 760 μm. In this process, for the purpose of controlling the adhesion of the interlayer film for a laminated glass, a magnesium acetate solution was added so that concentration of Mg in the interlayer film for a laminated glass was 65 ppm.

The laminated glass was produced in the same manner as in Example 1, except for the use of the obtained interlayer film for a laminated glass, and the same evaluations were made. Table 7 shows the results.

Examples 29 to 51, and Comparative Examples 16 to 18

Each of the interlayer films for a laminated glass was produced in the same manner as in Example 1, except that each of the compositions thereof was changed as shown in Table 7 and Table 8. The laminated glass was produced in the same manner as in Example 1, except for the use of the obtained interlayer film for a laminated glass, and the same evaluations were made.

TABLE 7

|  |  |  | Example | | | | | |
|---|---|---|---|---|---|---|---|---|
|  |  |  | 28 | 29 | 30 | 31 | 32 | 33 |
| Composition (parts by weight) | PVB |  | 100 | 100 | 100 | 100 | 100 | 100 |
|  | 4GO |  | 63 | 63 | 63 | 63 | 63 | 63 |
|  | Indole compound | A | 0.14 | 0.048 | 0.2 | — | — | — |
|  |  | B | — | — | — | 0.14 | 0.048 | 0.2 |
|  |  | C | — | — | — | — | — | — |
|  |  | D | — | — | — | — | — | — |
|  |  | E | — | — | — | — | — | — |
|  | Antioxidant |  | 0.4 | 0.4 | 0.4 | 0.4 | 0.4 | 0.4 |
|  | Ultraviolet absorber |  | 0.4 | 0.4 | 0.4 | 0.4 | 0.4 | 0.4 |
|  | ITO |  | 0 | 0 | 0 | 0 | 0 | 0 |
|  | Mg/ppm |  | 65 | 65 | 65 | 65 | 65 | 65 |
|  | Concentration of light absorber/weight % |  | 0.099 | 0.034 | 0.142 | 0.099 | 0.034 | 0.142 |
| Evaluation of transmittance | Transmittance/% | Ts | 78.5 | 78.2 | 78.9 | 78.3 | 78.4 | 78.5 |
|  |  | Tv | 88.4 | 88.4 | 88.8 | 88.2 | 88.5 | 88.3 |
|  | T(380-400 nm)/% | Before ultraviolet irradiation | 0.08 | 0.39 | 0.02 | 0.04 | 0.43 | 0.03 |
|  |  | After ultraviolet irradiation | 0.19 | 0.45 | 0.11 | 0.16 | 0.52 | 0.15 |
| Light exposure test | ΔE |  | 1.18 | 1.11 | 1.23 | 1.28 | 1.20 | 1.37 |
| Evaluation of preventive effect on pest insect attraction | The number of attracted winged insects |  | 4 | 4 | 8 | 5 | 2 | 1 |
| Evaluation of penetration resistance | 4 m |  | Pass | Pass | Pass | Pass | Pass | Pass |
|  | 5 m |  | Fail | Fail | Fail | Fail | Fail | Fail |
|  | 6 m |  | Fail | Fail | Fail | Fail | Fail | Fail |
| Durability test to heat | ΔE |  | 0.40 | 0.21 | 0.45 | 0.32 | 0.16 | 0.41 |
|  | The number of bubble less than 5 mm |  | 1 | 2 | 2 | 3 | 2 | 3 |
|  | The number of bubble greater than or equal to 5 mm, and less than 10 mm |  | 0 | 0 | 0 | 0 | 0 | 0 |
|  | The number of bubble greater than or equal to 10 mm |  | 0 | 0 | 0 | 0 | 0 | 0 |
|  | Presence of solid components |  | Absent | Absent | Absent | Absent | Absent | Absent |

TABLE 7-continued

|  |  |  | Example | | | Comparative Example | | |
| --- | --- | --- | --- | --- | --- | --- | --- | --- |
|  |  |  | 34 | 35 | 36 | 16 | 17 | 18 |
| Composition (parts by weight) | PVB |  | 100 | 100 | 100 | 100 | 100 | 100 |
|  | 4GO |  | 63 | 63 | 63 | 63 | 63 | 63 |
|  | Indole compound | A | — | — | — | — | — | — |
|  |  | B | — | — | — | — | — | — |
|  |  | C | 0.14 | 0.048 | 0.2 | — | — | — |
|  |  | D | — | — | — | 0.14 | — | — |
|  |  | E | — | — | — | — | 0.14 | — |
|  | Antioxidant |  | 0.4 | 0.4 | 0.4 | 0.4 | 0.4 | 0.4 |
|  | Ultraviolet absorber |  | 0.4 | 0.4 | 0.4 | 0.4 | 0.4 | 0.4 |
|  | ITO |  | 0 | 0 | 0 | 0 | 0 | 0 |
| Mg/ppm |  |  | 65 | 65 | 65 | 65 | 65 | 65 |
| Concentration of light absorber/weight % |  |  | 0.099 | 0.034 | 0.142 | 0.099 | 0.099 | 0.000 |
| Evaluation of transmittance | Transmittance/% | Ts | 78.4 | 78.9 | 78.3 | 78.2 | 78.6 | 78.7 |
|  |  | Tv | 88.2 | 88.7 | 88.6 | 88.5 | 88.4 | 88.5 |
|  | T(380-400 nm)/% | Before ultraviolet irradiation | 0.06 | 0.50 | 0.02 | 0.06 | 0.12 | 10.86 |
|  |  | After ultraviolet irradiation | 0.36 | 0.65 | 0.13 | 0.95 | 0.84 | 10.70 |
| Light exposure test | ΔE |  | 1.28 | 1.18 | 1.35 | 3.13 | 3.54 | 0.25 |
| Evaluation of preventive effect on pest insect attraction | The number of attracted winged insects |  | 3 | 6 | 4 | 2 | 7 | 30 |
| Evaluation of penetration resistance | 4 m |  | Pass | Pass | Pass | Pass | Pass | Pass |
|  | 5 m |  | Fail | Fail | Fail | Fail | Fail | Fail |
|  | 6 m |  | Fail | Fail | Fail | Fail | Fail | Fail |
| Durability test to heat | ΔE |  | 0.39 | 0.18 | 0.46 | 2.15 | 2.28 | 0.13 |
|  | The number of bubble less than 5 mm |  | 1 | 1 | 2 | 1 | 3 | 6 |
|  | The number of bubble greater than or equal to 5 mm, and less than 10 mm |  | 0 | 0 | 0 | 0 | 0 | 4 |
|  | The number of bubble greater than or equal to 10 mm |  | 0 | 0 | 0 | 0 | 0 | 0 |
|  | Presence of solid components |  | Absent | Absent | Absent | Absent | Absent | Absent |

TABLE 8

|  |  |  | Example | | | | | | | |
| --- | --- | --- | --- | --- | --- | --- | --- | --- | --- | --- |
|  |  |  | 37 | 38 | 39 | 40 | 41 | 42 | 43 | 44 |
| Composition (parts by weight) | PVB |  | 100 | 100 | 100 | 100 | 100 | 100 | 100 | 100 |
|  | 4GO |  | 63 | 63 | 63 | 63 | 63 | 63 | 63 | 63 |
|  | Indole compound | F | 0.14 | 0.048 | 0.2 | — | — | — | — | — |
|  |  | G | — | — | — | 0.14 | 0.048 | 0.2 | — | — |
|  |  | H | — | — | — | — | — | — | 0.14 | 0.048 |
|  |  | I | — | — | — | — | — | — | — | — |
|  |  | J | — | — | — | — | — | — | — | — |
|  | Antioxidant |  | 0.4 | 0.4 | 0.4 | 0.4 | 0.4 | 0.4 | 0.4 | 0.4 |
|  | Ultraviolet absorber |  | 0.4 | 0.4 | 0.4 | 0.4 | 0.4 | 0.4 | 0.4 | 0.4 |
|  | ITO |  | 0 | 0 | 0 | 0 | 0 | 0 | 0 | 0 |
| Mg/ppm |  |  | 65 | 65 | 65 | 65 | 65 | 65 | 65 | 65 |
| Concentration of light absorber/weight % |  |  | 0.099 | 0.034 | 0.142 | 0.099 | 0.034 | 0.142 | 0.099 | 0.034 |
| Evaluation of transmittance | Transmittance/% | Ts | 78.6 | 78.4 | 78.7 | 78.9 | 78.4 | 78.1 | 78.3 | 78.2 |
|  |  | Tv | 88.5 | 88.4 | 88.6 | 88.1 | 88.2 | 88.8 | 88.7 | 89.0 |
|  | T(380-400 nm)/% | Before ultraviolet irradiation | 0.08 | 0.42 | 0.03 | 0.06 | 0.51 | 0.02 | 0.09 | 0.48 |
|  |  | After ultraviolet irradiation | 0.15 | 0.65 | 0.14 | 0.18 | 0.73 | 0.11 | 0.20 | 0.68 |
| Light exposure test | ΔE |  | 1.16 | 0.99 | 1.30 | 1.25 | 1.19 | 1.41 | 1.29 | 0.91 |
| Evaluation of preventive effect on pest insect attraction | The number of attracted winged insects |  | 3 | 5 | 3 | 4 | 8 | 7 | 5 | 7 |
| Evaluation of penetration resistance | 4 m |  | Pass | Pass | Pass | Pass | Pass | Pass | Pass | Pass |
|  | 5 m |  | Fail | Fail | Fail | Fail | Fail | Fail | Fail | Fail |
|  | 6 m |  | Fail | Fail | Fail | Fail | Fail | Fail | Fail | Fail |
| Durability test to heat | ΔE |  | 0.41 | 0.25 | 0.62 | 0.42 | 0.23 | 0.48 | 0.46 | 0.30 |
|  | The number of bubble less than 5 mm |  | 2 | 1 | 2 | 3 | 2 | 1 | 3 | 4 |
|  | The number of bubble greater than or equal to 5 mm, and less than 10 mm |  | 0 | 0 | 0 | 0 | 0 | 0 | 0 | 0 |
|  | The number of bubble greater than or equal to 10 mm |  | 0 | 0 | 0 | 0 | 0 | 0 | 0 | 0 |
|  | Presence of solid components |  | Absent | Absent | Absent | Absent | Absent | Absent | Absent | Absent |

TABLE 8-continued

| | | | Example | | | | | | |
|---|---|---|---|---|---|---|---|---|---|
| | | | 45 | 46 | 47 | 48 | 49 | 50 | 51 |
| Composition (parts by weight) | | PVB | 100 | 100 | 100 | 100 | 100 | 100 | 100 |
| | | 4GO | 63 | 63 | 63 | 63 | 63 | 63 | 63 |
| | Indole compound | F | — | — | — | — | — | — | — |
| | | G | — | — | — | — | — | — | — |
| | | H | 0.2 | — | — | — | — | — | — |
| | | I | — | 0.14 | 0.048 | 0.2 | — | — | — |
| | | J | — | — | — | — | 0.14 | 0.048 | 0.2 |
| | Antioxidant | | 0.4 | 0.4 | 0.4 | 0.4 | 0.4 | 0.4 | 0.4 |
| | Ultraviolet absorber | | 0.4 | 0.4 | 0.4 | 0.4 | 0.4 | 0.4 | 0.4 |
| | ITO | | 0 | 0 | 0 | 0 | 0 | 0 | 0 |
| | Mg/ppm | | 65 | 65 | 65 | 65 | 65 | 65 | 65 |
| | Concentration of light absorber/weight % | | 0.142 | 0.099 | 0.034 | 0.142 | 0.099 | 0.034 | 0.142 |
| Evaluation of transmittance | Transmittance/% | Ts | 78.6 | 78.4 | 78.8 | 78.5 | 78.5 | 78.8 | 78.3 |
| | | Tv | 88.4 | 88.6 | 88.4 | 88.3 | 88.8 | 88.7 | 88.5 |
| | T(380-400 nm)/% | Before ultraviolet irradiation | 0.02 | 0.08 | 0.55 | 0.03 | 0.09 | 0.53 | 0.02 |
| | | After ultraviolet irradiation | 0.16 | 0.19 | 0.74 | 0.17 | 0.18 | 0.82 | 0.08 |
| Light exposure test | ΔE | | 1.32 | 1.09 | 0.85 | 1.37 | 1.24 | 1.11 | 1.30 |
| Evaluation of preventive effect on pest insect attraction | The number of attracted winged insects | | 6 | 5 | 5 | 2 | 7 | 4 | 6 |
| Evaluation of penetration resistance | 4 m | | Pass | Pass | Pass | Pass | Pass | Pass | Pass |
| | 5 m | | Fail | Fail | Fail | Fail | Fail | Fail | Fail |
| | 6 m | | Fail | Fail | Fail | Fail | Fail | Fail | Fail |
| Durability test to heat | ΔE | | 0.62 | 0.33 | 0.15 | 0.37 | 0.26 | 0.18 | 0.41 |
| | The number of bubble less than 5 mm | | 3 | 2 | 4 | 2 | 3 | 3 | 2 |
| | The number of bubble greater than or equal to 5 mm, and less than 10 mm | | 0 | 0 | 0 | 0 | 0 | 0 | 0 |
| | The number of bubble greater than or equal to 10 mm | | 0 | 0 | 0 | 0 | 0 | 0 | 0 |
| | Presence of solid components | | Absent | Absent | Absent | Absent | Absent | Absent | Absent |

Example 52

(1) Production of Resin Composition A

To 40 parts by weight of triethylene glycol di-2-ethylhexanoate (3GO) as a plasticizer were added 0.4 parts by weight of 2,6-di-t-butyl-p-cresol as an antioxidant, 0.4 parts by weight of an ultraviolet absorber ("TINUVIN 326" produced by Ciba Specialty Chemicals Inc.) having a benzotriazol structure, 0.14 parts by weight of the obtained indole compound A, and 0.28 parts by weight of tin-doped indium oxide particles (ITO) (volume average particle diameter: 35 nm). The resultant mixture was stirred by using a stirrer at 80° C. for 30 minutes to give a plasticizer solution.

The obtained plasticizer solution was sufficiently mixed with 100 parts by weight of polyvinyl butyral resin (PVB) (average polymerization degree: 1700, butyralation degree: 68.5 mol %, amount of the hydroxyl group: 30.6 mol %, amount of the acetyl group: 0.9 mol %) to produce a resin composition A. In this process, a magnesium acetate solution was added so that concentration of Mg in the resin composition A was 65 ppm.

(2) Production of Resin Composition B (Resin Layer B)

To 60 parts by weight of triethylene glycol di-2-ethylhexanoate (3GO) as a plasticizer were added 0.4 parts by weight of 2,6-di-t-butyl-p-cresol as an antioxidant, 0.4 parts by weight of an ultraviolet absorber ("TINUVIN 326" produced by Ciba Specialty Chemicals Inc.) having a benzotriazol structure, 0.14 parts by weight of the obtained indole compound A, and 0.28 parts by weight of tin-doped indium oxide particles (ITO) (volume average particle diameter: 35 nm). The resultant mixture was stirred by using a stirrer at 80° C. for 30 minutes to give a plasticizer solution.

The obtained plasticizer solution was sufficiently mixed with 100 parts by weight of polyvinyl butyral resin (PVB) (average polymerization degree: 2450, butyralation degree: 65.5 mol %, amount of the hydroxyl group: 20.1 mol %, amount of the acetyl group: 13.4 mol %) to produce a resin composition B.

(3) Production of Interlayer Film for Laminated Glass

The resin composition A and the resin composition B were co-extruded to produce an interlayer film for a laminated glass having a three-layer structure where a resin layer A (thickness: 330 μm), a resin layer B (thickness: 100 μm), and a resin layer A (thickness: 330 μm) were sequentially laminated.

The laminated glass was produced in the same manner as in Example 1, except for the use of the obtained interlayer film for a laminated glass, and the same evaluations were made.

Table 9 shows the results.

Examples 53 to 67, and Comparative Example 19

Each of the interlayer films for a laminated glass was produced in the same manner as in Example 1, except that each of the compositions thereof was changed as shown in Table 9 and Table 10. The laminated glass was produced in the same manner as in Example 1, except for the use of the obtained interlayer film for a laminated glass, and the same evaluations were made.

Table 9 and Table 10 show the results.

TABLE 9

| | | | Example | | | | | | Comparative Example |
|---|---|---|---|---|---|---|---|---|---|
| | | | 52 | 53 | 54 | 55 | 56 | 57 | 19 |
| Resin layer A | Composition (parts by weight) | PVB | 100 | 100 | 100 | 100 | 100 | 10 | 100 |
| | | Plasticizer (3GO) | 40 | 40 | 40 | 40 | 40 | 40 | 40 |
| | | Indole A | 0.14 | — | — | — | — | — | — |
| | | Indole B | — | — | 0.14 | — | — | — | — |
| | | Indole C | — | — | — | — | 0.14 | — | — |
| | | Antioxidant | 0.4 | 0.4 | 0.4 | 0.4 | 0.4 | 0.4 | 0.4 |
| | | Ultraviolet absorber | 0.4 | 0.4 | 0.4 | 0.4 | 0.4 | 0.4 | 0.4 |
| | | ITO | 0.28 | 0.28 | 0.28 | 0.28 | 0.28 | 0.28 | 0.28 |
| | | Mg/ppm | 65 | 65 | 65 | 65 | 65 | 65 | 65 |
| Resin layer B | Composition (parts by weight) | PVB | 100 | 100 | 100 | 100 | 100 | 100 | 100 |
| | | Plasticizer (3GO) | 60 | 60 | 60 | 60 | 60 | 60 | 60 |
| | | Indole A | 0.14 | 1.06 | — | — | — | — | — |
| | | Indole B | — | — | 0.14 | 1.06 | — | — | — |
| | | Indole C | — | — | — | — | 0.14 | 1.06 | — |
| | | Antioxidant | 0.4 | 0.4 | 0.4 | 0.4 | 0.4 | 0.4 | 0.4 |
| | | Ultraviolet absorber | 0.4 | 0.4 | 0.4 | 0.4 | 0.4 | 0.4 | 0.4 |
| | | ITO | 0.28 | 0.28 | 0.28 | 0.28 | 0.28 | 0.28 | 0.28 |
| Evaluation of transmittance | Transmittance/% | Ts | 66.3 | 66.8 | 65.8 | 66.0 | 66.5 | 66.2 | 67.7 |
| | | Tv | 87.2 | 87.8 | 87.4 | 87.4 | 87.7 | 87.9 | 87.3 |
| | T(380-400 nm)/% | Before ultraviolet irradiation | 0.05 | 0.06 | 0.05 | 0.09 | 0.06 | 0.05 | 10.16 |
| | | After ultraviolet irradiation | 0.20 | 0.37 | 0.26 | 0.41 | 0.24 | 0.35 | 10.08 |
| Light exposure test | | ΔE | 1.19 | 1.31 | 1.54 | 1.66 | 1.29 | 1.33 | 0.79 |
| Evaluation of preventive effect on pest insect attraction | The number of attracted winged insects | | 6 | 2 | 6 | 8 | 5 | 7 | 31 |
| Evaluation of penetration resistance | | 4 m | Pass | Pass | Pass | Pass | Pass | Pass | Pass |
| | | 5 m | Pass | Pass | Pass | Pass | Pass | Pass | Pass |
| | | 6 m | Pass | Pass | Pass | Pass | Pass | Pass | Pass |
| Durability test to heat | | ΔE | 0.42 | 0.55 | 0.44 | 0.41 | 0.53 | 0.61 | 0.21 |
| | The number of bubble less than 5 mm | | 2 | 0 | 2 | 0 | 3 | 0 | 0 |
| | The number of bubble greater than or equal to 5 mm, and less than 10 mm | | 0 | 7 | 0 | 12 | 0 | 5 | 8 |
| | The number of bubble greater than or equal to 10 mm | | 0 | 1 | 0 | 3 | 0 | 1 | 1 |
| | Presence of solid components | | Absent | Absent | Absent | Absent | Absent | Absent | Absent |

TABLE 10

| | | | Example | | | | | | | | | |
|---|---|---|---|---|---|---|---|---|---|---|---|---|
| | | | 58 | 59 | 60 | 61 | 62 | 63 | 64 | 65 | 66 | 67 |
| Resin layer A | Composition (parts by weight) | PVB | 100 | 100 | 100 | 100 | 100 | 100 | 100 | 100 | 100 | 100 |
| | | Plasticizer (3GO) | 40 | 40 | 40 | 40 | 40 | 40 | 40 | 40 | 40 | 40 |
| | | Indole F | 0.14 | — | — | — | — | — | — | — | — | — |
| | | Indole G | — | — | 0.14 | — | — | — | — | — | — | — |
| | | Indole H | — | — | — | — | 0.14 | — | — | — | — | — |
| | | Indole I | — | — | — | — | — | — | 0.14 | — | — | — |
| | | Indole J | — | — | — | — | — | — | — | — | 0.14 | — |
| | | Antioxidant | 0.4 | 0.4 | 0.4 | 0.4 | 0.4 | 0.4 | 0.4 | 0.4 | 0.4 | 0.4 |
| | | Ultraviolet absorber | 0.4 | 0.4 | 0.4 | 0.4 | 0.4 | 0.4 | 0.4 | 0.4 | 0.4 | 0.4 |
| | | ITO | 0.28 | 0.28 | 0.28 | 0.28 | 0.28 | 0.28 | 0.28 | 0.28 | 0.28 | 0.28 |
| | | Mg/ppm | 65 | 65 | 65 | 65 | 65 | 65 | 65 | 65 | 65 | 65 |
| Resin layer B | Composition (parts by weight) | PVB | 100 | 100 | 100 | 100 | 100 | 100 | 100 | 100 | 100 | 100 |
| | | Plasticizer (3GO) | 60 | 60 | 60 | 60 | 60 | 60 | 60 | 60 | 60 | 60 |
| | | Indole F | 0.14 | 1.06 | — | — | — | — | — | — | — | — |
| | | Indole G | — | — | 0.14 | 1.06 | — | — | — | — | — | — |
| | | Indole H | — | — | — | — | 0.14 | 1.06 | — | — | — | — |
| | | Indole I | — | — | — | — | — | — | 0.14 | 1.06 | — | — |
| | | Indole J | — | — | — | — | — | — | — | — | 0.14 | 1.06 |
| | | Antioxidant | 0.4 | 0.4 | 0.4 | 0.4 | 0.4 | 0.4 | 0.4 | 0.4 | 0.4 | 0.4 |
| | | Ultraviolet absorber | 0.4 | 0.4 | 0.4 | 0.4 | 0.4 | 0.4 | 0.4 | 0.4 | 0.4 | 0.4 |
| | | ITO | 0.28 | 0.28 | 0.28 | 0.28 | 0.28 | 0.28 | 0.28 | 0.28 | 0.28 | 0.28 |
| Evaluation of transmittance | Transmittance/% | Ts | 66.9 | 66.3 | 66.2 | 66.7 | 66.6 | 66.5 | 66.4 | 66.8 | 66.1 | 66.4 |
| | | Tv | 87.5 | 87.4 | 87.8 | 87.2 | 87.8 | 87.6 | 87.9 | 87.7 | 87.8 | 87.5 |
| | T(380-400 nm)/% | Before ultraviolet irradiation | 0.08 | 0.05 | 0.04 | 0.03 | 0.07 | 0.03 | 0.06 | 0.04 | 0.06 | 0.06 |
| | | After ultraviolet irradiation | 0.25 | 0.36 | 0.27 | 0.30 | 0.25 | 0.36 | 0.28 | 0.33 | 0.29 | 0.31 |

TABLE 10-continued

|  |  | Example |  |  |  |  |  |  |  |  |  |
|---|---|---|---|---|---|---|---|---|---|---|---|
|  |  | 58 | 59 | 60 | 61 | 62 | 63 | 64 | 65 | 66 | 67 |
| Light exposure test | ΔE | 1.28 | 1.30 | 1.45 | 1.49 | 1.38 | 1.41 | 1.32 | 1.36 | 1.41 | 1.51 |
| Evaluation of preventive effect on pest insect attraction | The number of attracted winged insects | 6 | 5 | 2 | 7 | 8 | 2 | 4 | 6 | 8 | 3 |
| Evaluation of penetration resistance | 4 m | Pass | Pass | Pass | Pass | Pass | Pass | Pass | Pass | Pass | Pass |
|  | 5 m | Pass | Pass | Pass | Pass | Pass | Pass | Pass | Pass | Pass | Pass |
|  | 6 m | Pass | Pass | Pass | Pass | Pass | Pass | Pass | Pass | Pass | Pass |
| Durability test to heat | ΔE | 0.87 | 0.96 | 0.95 | 0.91 | 0.87 | 0.83 | 1.14 | 1.04 | 0.90 | 0.93 |
|  | The number of bubble less than 5 mm | 1 | 0 | 1 | 0 | 3 | 0 | 1 | 0 | 2 | 0 |
|  | The number of bubble greater than or equal to 5 mm, and less than 10 mm | 0 | 15 | 0 | 7 | 0 | 5 | 0 | 4 | 0 | 6 |
|  | The number of bubble greater than or equal to 10 mm | 0 | 2 | 0 | 1 | 0 | 1 | 0 | 1 | 0 | 3 |
| Presence of solid components |  | Absent | Absent | Absent | Absent | Absent | Absent | Absent | Absent | Absent | Absent |

Example 68

To 49 parts by weight of triethylene glycol-di-2-ethylhexanoate (3GO) as a plasticizer were added 0.4 parts by weight of 2,6-di-t-butyl-p-cresol (BHT) as an antioxidant, 0.4 parts by weight of an ultraviolet absorber ("TINUVIN 326" produced by Ciba Specialty Chemicals Inc.) having a benzotriazol structure, and 0.14 parts by weight of the obtained indole compound A. The resultant mixture was stirred by using a stirrer at 80° C. for 30 minutes to give a plasticizer solution.

The obtained plasticizer solution was sufficiently mixed with 100 parts by weight of polyvinyl butyral resin (PVB) (average polymerization degree: 2450, butyralation degree: 65.5 mol %, amount of the hydroxyl group: 20.1 mol %, amount of the acetyl group: 13.4 mol %). Then, a twin-screw aeolotropic extruder was used to produce an interlayer film for a laminated glass having a film thickness of 760 μm. In this process, a magnesium acetate solution was added so that concentration of Mg in the interlayer film for a laminated glass was 65 ppm.

The laminated glass was produced in the same manner as in Example 1, except for the use of the obtained interlayer film for a laminated glass, and the same evaluations were made.

Table 11 shows the results.

Examples 69 to 91, and Comparative Examples 20 to 22

Each of the interlayer films for a laminated glass was produced in the same manner as in Example 1, except that each of the compositions thereof was changed as shown in Table 11 and Table 12. The laminated glass was produced in the same manner as in Example 1, except for the use of the obtained interlayer film for a laminated glass, and the same evaluations were made.

Table 11 and Table 12 show the results.

TABLE 11

|  |  |  | Example |  |  |  |  |  |
|---|---|---|---|---|---|---|---|---|
|  |  |  | 68 | 69 | 70 | 71 | 72 | 73 |
| Composition (parts by weight) | PVB |  | 100 | 100 | 100 | 100 | 100 | 100 |
|  | 3GO |  | 49 | 49 | 49 | 49 | 49 | 49 |
|  | Indole compound | A | 0.14 | 0.048 | 0.2 | — | — | — |
|  |  | B | — | — | — | 0.14 | 0.048 | 0.2 |
|  |  | C | — | — | — | — | — | — |
|  |  | D | — | — | — | — | — | — |
|  |  | E | — | — | — | — | — | — |
|  | Antioxidant |  | 0.4 | 0.4 | 0.4 | 0.4 | 0.4 | 0.4 |
|  | Ultraviolet absorber |  | 0.4 | 0.4 | 0.4 | 0.4 | 0.4 | 0.4 |
|  | ITO |  | 0 | 0 | 0 | 0 | 0 | 0 |
|  | Mg/ppm |  | 65 | 65 | 65 | 65 | 65 | 65 |
| Concentration of light absorber/weight % |  |  | 0.099 | 0.034 | 0.142 | 0.099 | 0.034 | 0.142 |
| Evaluation of transmittance | Transmittance/% | Ts | 78.4 | 78.6 | 78.8 | 78.2 | 78.2 | 78.6 |
|  |  | Tv | 88.6 | 88.3 | 88.6 | 88.2 | 88.4 | 88.3 |
|  | T(380-400 nm)/% | Before ultraviolet irradiation | 0.05 | 0.32 | 0.02 | 0.05 | 0.39 | 0.02 |
|  |  | After ultraviolet irradiation | 0.18 | 0.46 | 0.15 | 0.23 | 0.44 | 0.14 |
| Light exposure test | ΔE |  | 1.17 | 1.05 | 1.22 | 1.29 | 1.18 | 1.27 |
| Evaluation of preventive effect on pest insect attraction | The number of attracted winged insects |  | 8 | 3 | 5 | 4 | 2 | 4 |
| Evaluation of penetration resistance | 4 m |  | Pass | Pass | Pass | Pass | Pass | Pass |
|  | 5 m |  | Pass | Pass | Pass | Pass | Pass | Pass |
|  | 6 m |  | Fail | Fail | Fail | Fail | Fail | Fail |
| Durability test to heat | ΔE |  | 0.44 | 0.23 | 0.44 | 0.32 | 0.18 | 0.37 |
|  | The number of bubble less than 5 mm |  | 3 | 2 | 1 | 1 | 2 | 3 |
|  | The number of bubble greater than or equal to 5 mm, and less than 10 mm |  | 0 | 0 | 0 | 0 | 0 | 0 |
|  | The number of bubble greater than or equal to 10 mm |  | 0 | 0 | 0 | 0 | 0 | 0 |

TABLE 11-continued

| | | | | | | | |
|---|---|---|---|---|---|---|---|
| Presence of solid components | | Absent | Absent | Absent | Absent | Absent | Absent |

| | | Example | | | Comparative Example | | |
|---|---|---|---|---|---|---|---|
| | | 74 | 75 | 76 | 20 | 21 | 22 |
| Composition (parts by weight) | PVB | 100 | 100 | 100 | 100 | 100 | 100 |
| | 3GO | 49 | 49 | 49 | 49 | 49 | 49 |
| | Indole compound A | — | — | — | — | — | — |
| | B | — | — | — | — | — | — |
| | C | 0.14 | 0.048 | 0.2 | — | — | — |
| | D | — | — | — | 0.14 | — | — |
| | E | — | — | — | — | 0.14 | — |
| | Antioxidant | 0.4 | 0.4 | 0.4 | 0.4 | 0.4 | 0.4 |
| | Ultraviolet absorber | 0.4 | 0.4 | 0.4 | 0.4 | 0.4 | 0.4 |
| | ITO | 0 | 0 | 0 | 0 | 0 | 0 |
| Mg/ppm | | 65 | 65 | 65 | 65 | 65 | 65 |
| Concentration of light absorber/weight % | | 0.099 | 0.034 | 0.142 | 0.099 | 0.099 | 0.000 |
| Evaluation of transmittance | Transmittance/% Ts | 78.4 | 78.6 | 78.5 | 78.4 | 78.8 | 78.8 |
| | Tv | 88.2 | 88.6 | 88.4 | 88.5 | 88.6 | 88.3 |
| | T(380-400 nm)/% Before ultraviolet irradiation | 0.09 | 0.47 | 0.03 | 0.08 | 0.10 | 10.72 |
| | After ultraviolet irradiation | 0.36 | 0.63 | 1.18 | 1.16 | 0.96 | 10.94 |
| Light exposure test | ΔE | 1.36 | 1.23 | 1.39 | 3.31 | 3.82 | 0.25 |
| Evaluation of preventive effect on pest insect attraction | The number of attracted winged insects | 5 | 2 | 3 | 4 | 6 | 36 |
| Evaluation of penetration resistance | 4 m | Pass | Pass | Pass | Pass | Pass | Pass |
| | 5 m | Pass | Pass | Pass | Pass | Pass | Pass |
| | 6 m | Fail | Fail | Fail | Fail | Fail | Fail |
| Durability test to heat | ΔE | 0.40 | 0.19 | 0.51 | 1.87 | 2.41 | 0.20 |
| | The number of bubble less than 5 mm | 1 | 2 | 2 | 1 | 1 | 5 |
| | The number of bubble greater than or equal to 5 mm, and less than 10 mm | 0 | 0 | 0 | 0 | 0 | 7 |
| | The number of bubble greater than or equal to 10 mm | 0 | 0 | 0 | 0 | 0 | 0 |
| Presence of solid components | | Absent | Absent | Absent | Absent | Absent | Absent |

TABLE 12

| | | Example | | | | | | | |
|---|---|---|---|---|---|---|---|---|---|
| | | 77 | 78 | 79 | 80 | 81 | 82 | 83 | 84 |
| Composition (parts by weight) | PVB | 100 | 100 | 100 | 100 | 100 | 100 | 100 | 100 |
| | 3GO | 49 | 49 | 49 | 49 | 49 | 49 | 49 | 49 |
| | Indole compound F | 0.14 | 0.048 | 0.2 | — | — | — | — | — |
| | G | — | — | — | 0.14 | 0.048 | 0.2 | — | — |
| | H | — | — | — | — | — | — | 0.14 | 0.048 |
| | I | — | — | — | — | — | — | — | — |
| | J | — | — | — | — | — | — | — | — |
| | Antioxidant | 0.4 | 0.4 | 0.4 | 0.4 | 0.4 | 0.4 | 0.4 | 0.4 |
| | Ultraviolet absorber | 0.4 | 0.4 | 0.4 | 0.4 | 0.4 | 0.4 | 0.4 | 0.4 |
| | ITO | 0 | 0 | 0 | 0 | 0 | 0 | 0 | 0 |
| Mg/ppm | | 65 | 65 | 65 | 65 | 65 | 65 | 65 | 65 |
| Concentration of light absorber/weight % | | 0.099 | 0.034 | 0.142 | 0.099 | 0.034 | 0.142 | 0.099 | 0.034 |
| Evaluation of transmittance | Transmittance/% Ts | 78.8 | 78.3 | 78.4 | 78.4 | 78.9 | 78.5 | 78.4 | 78.2 |
| | Tv | 88.6 | 88.5 | 88.2 | 88.4 | 88.6 | 88.7 | 88.3 | 88.8 |
| | T(380-400 nm)/% Before ultraviolet irradiation | 0.09 | 0.46 | 0.02 | 0.08 | 0.50 | 0.02 | 0.09 | 0.51 |
| | After ultraviolet irradiation | 0.18 | 0.58 | 0.15 | 0.23 | 0.77 | 0.09 | 0.20 | 0.66 |
| Light exposure test | ΔE | 1.15 | 0.87 | 1.34 | 1.28 | 1.21 | 1.38 | 1.29 | 0.99 |
| Evaluation of preventive effect on pest insect attraction | The number of attracted winged insects | 2 | 8 | 1 | 6 | 5 | 4 | 2 | 3 |
| Evaluation of penetration resistance | 4 m | Pass | Pass | Pass | Pass | Pass | Pass | Pass | Pass |
| | 5 m | Pass | Pass | Pass | Pass | Pass | Pass | Pass | Pass |
| | 6 m | Fail | Fail | Fail | Fail | Fail | Fail | Fail | Fail |
| Durability test to heat | ΔE | 0.39 | 0.25 | 0.66 | 0.48 | 0.30 | 0.55 | 0.41 | 0.28 |
| | The number of bubble less than 5 mm | 2 | 2 | 2 | 3 | 1 | 3 | 2 | 3 |
| | The number of bubble greater than or equal to 5 mm, and less than 10 mm | 0 | 0 | 0 | 0 | 0 | 0 | 0 | 0 |
| | The number of bubble greater than or equal to 10 mm | 0 | 0 | 0 | 0 | 0 | 0 | 0 | 0 |
| Presence of solid components | | Absent | Absent | Absent | Absent | Absent | Absent | Absent | Absent |

TABLE 12-continued

| | | | Example | | | | | | |
|---|---|---|---|---|---|---|---|---|---|
| | | | 85 | 86 | 87 | 88 | 89 | 90 | 91 |
| Composition (parts by weight) | | PVB | 100 | 100 | 100 | 100 | 100 | 100 | 100 |
| | | 3GO | 49 | 49 | 49 | 49 | 49 | 49 | 49 |
| | Indole compound | F | — | — | — | — | — | — | — |
| | | G | — | — | — | — | — | — | — |
| | | H | 0.2 | — | — | — | — | — | — |
| | | I | — | 0.14 | 0.048 | 0.2 | — | — | — |
| | | J | — | — | — | — | 0.14 | 0.048 | 0.2 |
| | Antioxidant | | 0.4 | 0.4 | 0.4 | 0.4 | 0.4 | 0.4 | 0.4 |
| | Ultraviolet absorber | | 0.4 | 0.4 | 0.4 | 0.4 | 0.4 | 0.4 | 0.4 |
| | ITO | | 0 | 0 | 0 | 0 | 0 | 0 | 0 |
| Mg/ppm | | | 65 | 65 | 65 | 65 | 65 | 65 | 65 |
| Concentration of light absorber/weight % | | | 0.142 | 0.099 | 0.034 | 0.142 | 0.099 | 0.034 | 0.142 |
| Evaluation of transmittance | Transmittance/% | Ts | 78.6 | 78.5 | 78.3 | 78.5 | 78.6 | 78.4 | 78.8 |
| | | Tv | 88.3 | 88.8 | 88.4 | 88.3 | 88.8 | 88.5 | 88.2 |
| | T(380-400 nm)/% | Before ultraviolet irradiation | 0.03 | 0.07 | 0.61 | 0.03 | 0.10 | 0.61 | 0.03 |
| | | After ultraviolet irradiation | 0.18 | 0.26 | 0.77 | 0.18 | 0.32 | 0.86 | 0.18 |
| Light exposure test | ΔE | | 1.31 | 1.14 | 0.95 | 1.36 | 1.28 | 1.21 | 1.46 |
| Evaluation of preventive effect on pest insect attraction | The number of attracted winged insects | | 7 | 5 | 5 | 2 | 6 | 3 | 4 |
| Evaluation of penetration resistance | 4 m | | Pass | Pass | Pass | Pass | Pass | Pass | Pass |
| | 5 m | | Pass | Pass | Pass | Pass | Pass | Pass | Pass |
| | 6 m | | Fail | Fail | Fail | Fail | Fail | Fail | Fail |
| Durability test to heat | ΔE | | 0.46 | 0.28 | 0.19 | 0.42 | 0.28 | 0.22 | 0.32 |
| | The number of bubble less than 5 mm | | 1 | 2 | 1 | 2 | 3 | 1 | 1 |
| | The number of bubble greater than or equal to 5 mm, and less than 10 mm | | 0 | 0 | 0 | 0 | 0 | 0 | 0 |
| | The number of bubble greater than or equal to 10 mm | | 0 | 0 | 0 | 0 | 0 | 0 | 0 |
| Presence of solid components | | | Absent | Absent | Absent | Absent | Absent | Absent | Absent |

INDUSTRIAL APPLICABILITY

According to the present invention, it is possible to provide an interlayer film for a laminated glass which can reduce transmittance of ultraviolet rays having wavelength of 380 to 400 nm and has excellent durability to light exposure while maintaining high visible light transmittance.

The invention claimed is:

1. An interlayer film for a laminated glass,
which comprises a polyvinyl acetal resin, a plasticizer and an indole compound having a structure represented by the following general Chemical Formula (1):

[Chemical Formula 1]

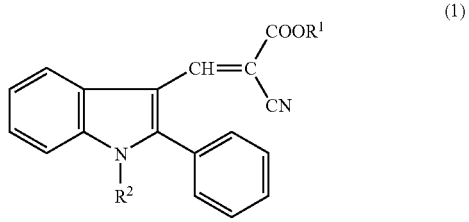

(1)

wherein $R^1$ represents an alkyl group having 1 to 3 of carbon atoms, and $R^2$ represents hydrogen, an alkyl group having 1 to 10 of carbon atoms, or an aralkyl group having 7 to 10 of carbon atoms, and which provides improved durability to light exposure and improved reduced transmittance of ultraviolet light having wavelength of 380 to 400 nm as compared to indoles of Chemical Formula 1, wherein $R^1$ is an alkyl group of greater than 3 carbon atoms and while maintaining visible light transmittance.

2. The interlayer film for a laminated glass according to claim 1, wherein $R^1$ represents methyl group in the indole compound having a structure represented by the general Chemical Formula (1).

3. The interlayer film for a laminated glass according to claim 2, which comprises a multilayer laminated structure comprising at least two resin layers, said at least two resin layers including an indole compound-containing resin layer, said indole compound-containing resin layer comprising the polyvinyl acetal resin, the plasticizer and the indole compound having a structure represented by the general Chemical Formula (1).

4. The interlayer film for a laminated glass according to claim 1, wherein the content of the indole compound is 0.030 to 0.145 weight % in the interlayer film.

5. The interlayer film for a laminated glass according to claim 4, which comprises a multilayer laminated structure comprising at least two resin layers, said at least two resin layers including an indole compound-containing resin layer, said indole compound-containing resin layer comprising the polyvinyl acetal resin, the plasticizer and the indole compound having a structure represented by the general Chemical Formula (1).

6. The interlayer film for a laminated glass according to claim 1, wherein the plasticizer is triethylene glycol di-2-ethylhexanoate.

7. The interlayer film for a laminated glass according to claim 6, which comprises a multilayer laminated structure comprising at least two resin layers, said at least two resin layers including an indole compound-containing resin layer, said indole compound-containing resin layer comprising the polyvinyl acetal resin, the plasticizer and the indole compound having a structure represented by the general Chemical Formula (1).

8. The interlayer film for a laminated glass according to claim 1, which further comprises an infrared absorber.

9. The interlayer film for a laminated glass according to claim 8,
wherein the infrared absorber is a tin-doped indium oxide particle.

10. The interlayer film for a laminated glass according to claim 8, which comprises a multilayer laminated structure comprising at least two resin layers, said at least two resin layers including an indole compound-containing resin layer, said indole compound-containing resin layer comprising the polyvinyl acetal resin, the plasticizer and the indole compound having a structure represented by the general Chemical Formula (1).

11. The interlayer film for a laminated glass according to claim 1, which comprises a multilayer laminated structure comprising at least two resin layers, wherein at least an outermost layer of said at least two resin layers is an indole compound-containing resin layer, said indole compound-containing resin layer comprising the polyvinyl acetal resin, the plasticizer and the indole compound having a structure represented by the general Chemical Formula (1).

12. The interlayer film for a laminated glass according to claim 1, wherein the reduced transmittance of ultraviolet light having wavelength of 380 to 400 nm is 0.5% or less after exposure.

13. The interlayer film for a laminated glass according to claim 1, which maintains visible light transmittance of at least 60%.

14. The interlayer film for a laminated glass according to claim 1, which maintains visible light transmittance of at least 70%.

15. The interlayer film for a laminated glass according to claim 1, which maintains visible light transmittance of at least 75%.

16. The interlayer film for a laminated glass according to claim 1, which maintains visible light transmittance of at least 80%.

17. The interlayer film for a laminated glass according to claim 1 having a durability to light exposure whereby the color difference ΔE is 1.65 or less.

18. The interlayer film for a laminated glass according to claim 1, wherein the content of the plasticizer is 30 parts by weight to 70 parts by weight per 100 parts by weight of the polyvinyl acetal.

19. The interlayer film for a laminated glass according to claim 1, wherein the content of the plasticizer is 50 parts by weight to 70 parts by weight per 100 parts by weight of the polyvinyl acetal.

20. The interlayer film for a laminated glass according to claim 1, wherein the interlayer film has a thickness of 0.1 mm to 3 mm.

21. A laminated glass, wherein the interlayer film for a laminated glass according to claim 1 is sandwiched between two sheets of glasses.

22. A laminated glass, wherein the interlayer film for a laminated glass according to claim 2 is sandwiched between two sheets of glasses.

23. A laminated glass, wherein the interlayer film for a laminated glass according to claim 4 is sandwiched between two sheets of glasses.

24. A laminated glass, wherein the interlayer film for a laminated glass according to claim 6 is sandwiched between two sheets of glasses.

25. A laminated glass, wherein the interlayer film for a laminated glass according to claim 8 is sandwiched between two sheets of glasses.

26. A laminated glass, wherein the interlayer film for a laminated glass according to claim 9 is sandwiched between two sheets of glasses.

27. A laminated glass, wherein the interlayer film for a laminated glass according to claim 11 is sandwiched between two sheets of glasses.

28. A laminated glass, wherein the interlayer film for a laminated glass according to claim 3 is sandwiched between two sheets of glasses.

29. A laminated glass, wherein the interlayer film for a laminated glass according to claim 5 is sandwiched between two sheets of glasses.

30. A laminated glass, wherein the interlayer film for a laminated glass according to claim 7 is sandwiched between two sheets of glasses.

31. A laminated glass, wherein the interlayer film for a laminated glass according to claim 10 is sandwiched between two sheets of glasses.

* * * * *